United States Patent [19]
Lee et al.

[11] Patent Number: 5,837,240
[45] Date of Patent: Nov. 17, 1998

[54] MULTIMERIC, RECOMBINANT UREASE VACCINE

[75] Inventors: Cynthia K. Lee, Needham; Thomas P. Monath, Harvard; Samuel K. Ackerman, Weston; William D. Thomas, Winchester; Gopalan Soman, Belmont; Harold Kleanthous, Allston; Richard A. Weltzin, Lunenburg; Jacques Pappo, Newton; Thomas Ermak, Brookline; Farshad Guirakhoo, Melrose; Hitesh Bhagat, Framingham; Ilene Sussman, Newton, all of Mass.

[73] Assignee: OraVax-Merieux Co., Cambridge, Mass.

[21] Appl. No.: 920,095

[22] Filed: Aug. 26, 1997

Related U.S. Application Data

[63] Continuation of Ser. No. 431,041, Apr. 28, 1995, abandoned.
[51] Int. Cl.⁶ .......................... A61K 38/46; A61K 39/02; A61K 39/106
[52] U.S. Cl. ...................... 424/94.6; 424/234.1; 435/227; 514/925; 514/926; 514/927
[58] Field of Search ................................ 424/94.6, 234.1; 435/227, 195; 514/925, 926, 927

[56] References Cited

FOREIGN PATENT DOCUMENTS

WO 94/09823  5/1994  WIPO .

OTHER PUBLICATIONS

Michetti, P. et al., *Gastroenterology* 107(4):1002–1011 (1994).
Davin, C. et al., *Gastroenterology* 104(4):A1035 (1993).
Pallen, M.J. et al., *Lancet* 336:156–157 (1990).
Hu, Li–Tai et al., Infection and Immunity, vol. 60, No. 7, (Jul. 1992), pp. 2657–2666.

*Primary Examiner*—Dian C. Jacobson
*Attorney, Agent, or Firm*—Clark & Elbing LLP

[57] ABSTRACT

Methods and compositions are provided for prophylactic and antibacterial therapy for Helicobacter, particularly for *Helicobacter pylori*, infection of humans. The immunogenic composition of the invention is composed of a plurality of multimeric complexes, each complex being composed of recombinant, enzymatically inactive *Helicobacter pylori* urease. Each multimeric complex is composed of six Urease A subunits and six Urease B subunits. Alternatively, the composition is composed of a mixture of multimeric complexes, wherein each multimeric complex in the mixture is composed of six Urease A subunits and six Urease B subunits or four Urease A subunits and four Urease B subunits.

10 Claims, 20 Drawing Sheets

```
                              T7 promoter    ──────►        Lac Operator
1                   TAATACGACTCACTATAGGGGAATTGTGAGCGGATAACAATTC
                    (BL 1 primer)
44   CCCTCTAGGATCCACCTTGATTGCGTTATGTCTTCAAGGAAAAACACTTTAAGAATAGGAGAATGAG
Start UreA    BamHI                                             RBS
      Met Lys Leu Thr Pro Lys Glu Leu Asp Lys Leu Met Leu His Tyr Ala Gly 17
111   ATG AAA CTC ACC CCA AAA GAG TTA GAC AAG TTG ATG CTC CAC TAC GCT GGA Glu Leu Ala Lys Lys Arg Lys Glu Lys Gly Ile Lys Leu Asn Tyr Val Glu 34
163   GAA TTA GCT AAA AAA CGC AAA GAA AAA GGC ATT AAG CTT AAC TAT GTG GAA Ala Val Ala Leu Ile Ser Ala His Ile Met Glu Glu Ala Arg Ala Gly Lys 51
214   GCG GTA GCT TTG ATT AGT GCC CAT ATT ATG GAA GAA GCG AGA GCT GGT AAA Lys Thr Ala Ala Glu Leu Met Gln Glu Gly Arg Thr Leu Leu Lys Pro Asp 68
265   AAG ACT GCG GCT GAA TTG ATG CAA GAA GGG CGC ACT CTT TTA AAA CCG GAT Asp Val Met Asp Gly Val Ala Ser Met Ile His Glu Val Gly Ile Glu Ala 85
316   GAT GTG ATG GAT GGC GTG GCA AGC ATG ATC CAT GAA GTG GGT ATT GAA GCG Met Phe Pro Asp Gly Thr Lys Leu Val Thr Val His Thr Pro Ile Glu Ala 102
367   ATG TTT CCT GAT GGG ACC AAA CTC GTA ACC GTG CAT ACC CCT ATT GAG GCC Asn Gly Lys Leu Val Pro Gly Glu Leu Phe Leu Lys Asn Glu Asp Ile Thr 119
418   AAT GGT AAA TTA GTT CCT GGT GAG TTG TTC TTA AAA AAT GAA GAC ATC ACT Thr Asn Glu Gly Lys Lys Ala Val Ser Val Lys Val Lys Asn Val Gly Asp 136
469   ACT AAC GAA GGC AAA AAA GCC GTT AGC GTG AAA GTT AAA AAT GTT GGC GAC Arg Pro Val Gln Ile Gly Ser His Phe His Phe Phe Glu Val Asn Arg Cys 153
520   AGA CCG GTT CAA ATC GGC TCA CAC TTC CAT TTC TTT GAA GTG AAT AGA TGC Leu Asp Phe Asp Arg Glu Lys Thr Phe Gly Lys Arg Leu Asp Ile Ala Ser 170
571   TTA GAC TTT GAC AGA GAA AAA ACT TTC GGT AAA CGC TTA GAC ATT GCG AGC Gly Thr Ala Val Arg Phe Glu Pro Gly Glu Glu Lys Ser Val Glu Leu Ile 187
622   GGG ACA GCG GTA AGG TTT GAG CCT GGC GAA GAA AAA TCC GTA GAG TTG ATT Asp Ile Gly Gly Asn Arg Arg Ile Phe Gly Phe Asn Ala Leu Val Asp Arg 204
673   GAC ATT GGC GGT AAC AGA AGA ATC TTT GGA TTT AAC GCG TTG GTT GAT AGG Gln Ala Asp Asn Glu Ser Lys Lys Ile Ala Leu His Arg Ala Lys Glu Arg 221
724   CAA GCC GAT AAC GAA AGC AAA AAA ATT GCT TTA CAC AGA GCT AAA GAG CGT Gly Phe His Gly Ala Lys Ser Asp Asp Asn Tyr Val Lys Thr Ile Lys Glu 238
775   GGT TTT CAT GGC GCT AAA AGC GAT GAC AAC TAT GTA AAA ACA ATT AA G GAG
                                                                        RBS
      Stop
826   TAA GAA                    Fig. 3A
```

Start UreB

```
         Met Lys Lys Ile Ser Arg Lys Glu Tyr Ala Ser Met Tyr Gly Pro Thr Thr  17
   831   ATG AAA AAG ATT AGC AGA AAA GAA TAT GCT TCT ATG TAT GGC CCT ACT ACA

Gly Asp Lys Val Arg Leu Gly Asp Thr Asp Leu Ile Ala Glu Val Glu His  34
   863   GGC GAT AAA GTG AGA TTG GGC GAT ACA GAC TTG ATC GCT GAA GTA GAA CAT

Asp Tyr Thr Ile Tyr Gly Glu Glu Leu Lys Phe Gly Gly Gly Lys Thr Leu  51
   934   GAC TAC ACC ATT TAT GGC GAA GAG CTT AAA TTC GGC GGC GGT AAA ACC CTA

Arg Glu Gly Met Ser Gln Ser Asn Asn Pro Ser Lys Glu Glu Leu Asp Leu  68
   985   AGA GAA GGC ATG AGC CAA TCT AAC AAC CCT AGC AAA GAA GAA CTG GAT CTA

Ile Ile Thr Asn Ala Leu Ile Val Asp Tyr Thr Gly Ile Tyr Lys Ala Asp  85
  1036   ATC ATC ACT AAC GCT TTA ATC GTG GAT TAC ACC GGT ATT TAT AAA GCG GAT

Ile Gly Ile Lys Asp Gly Lys Ile Ala Gly Ile Gly Lys Gly Gly Asn Lys 102
  1087   ATT GGT ATT AAA GAT GGC AAA ATC GCT GGC ATT GGT AAA GGC GGT AAC AAA

Asp Thr Gln Asp Gly Val Lys Asn Asn Leu Ser Val Gly Pro Ala Thr Glu 119
  1138   GAC ACG CAA GAT GGC GTT AAA AAC AAT CTT AGC GTG GGT CCT GCT ACT GAA

Ala Leu Ala Gly Glu Gly Leu Ile Val Thr Ala Gly Gly Ile Asp Thr His 136
  1189   GCC TTA GCC GGT GAA GGT TTG ATT GTA ACT GCT GGT GGT ATT GAC ACA CAC

Ile His Phe Ile Ser Pro Gln Gln Ile Pro Thr Ala Phe Ala Ser Gly Val 153
  1240   ATC CAC TTC ATC TCC CCC CAA CAA ATC CCT ACA GCT TTT GCA AGC GGT GTA

Thr Thr Met Ile Gly Gly Gly Thr Gly Pro Ala Asp Gly Thr Asn Ala Thr 170
  1291   ACA ACC ATG ATT GGT GGC GGA ACT GGC CCT GCT GAT GGC ACT AAC GCA ACC

Thr Ile Thr Pro Gly Arg Arg Asn Leu Lys Phe Met Leu Arg Ala Ala Glu 187
  1342   ACT ATC ACT CCA GGT AGA AGA AAT TTA AAA TTC ATG CTC AGA GCG GCT GAA

Glu Tyr Ser Met Asn Phe Gly Phe Leu Ala Lys Gly Asn Ala Ser Asn Asp 204
  1393   GAA TAT TCT ATG AAC TTT GGT TTC TTG GCT AAA GGT AAC GCT TCT AAC GAT

Ala Ser Leu Ala Asp Gln Ile Glu Ala Gly Ala Ile Gly Leu Lys Ile His 221
  1444   GCA AGC TTA GCC GAC CAA ATT GAA GCT GGT GCG ATT GGC CTT AAA ATC CAC

Glu Asp Trp Gly Thr Thr Pro Ser Ala Ile Asn His Ala Leu Asp Val Ala 238
  1495   GAA GAC TGG GGG ACC ACT CCT TCT GCA ATC AAT CAT GCG TTA GAT GTT GCG

Asp Lys Tyr Asp Val Gln Val Ala Ile His Thr Asp Thr Leu Asn Glu Ala 255
  1546   GAC AAA TAC GAT GTG CAA GTC GCT ATC CAC ACA GAC ACT TTG AAT GAA GCC

Gly Cys Val Glu Asp Thr Met Ala Ala Ile Ala Gly Arg Thr Met His Thr 272
  1597   GGT TGC GTG GAA GAC ACT ATG GCA GCT ATT GCC GGA CGC ACT ATG CAC ACT
```

Fig. 3B

```
        Tyr His Thr Glu Gly Ala Gly Gly Gly His Ala Pro Asp Ile Ile Lys Val 289
1648    TAC CAC ACT GAA GGC GCT GGC GGC GGA CAC GCT CCT GAT ATT ATT AAA GTG

Ala Gly Glu His Asn Ile Leu Pro Ala Ser Thr Asn Pro Thr Ile Pro Phe 306
1699    GCC GGT GAA CAC AAC ATC CTA CCC GCT TCC ACT AAC CCC ACT ATC CCT TTC

Thr Val Asn Thr Glu Ala Glu His Met Asp Met Leu Met Val Cys His His 323
1750    ACC GTG AAT ACA GAA GCC GAA CAC ATG GAC ATG CTT ATG GTG TGC CAC CAC

Leu Asp Lys Ser Ile Lys Glu Asp Val Gln Phe Ala Asp Ser Arg Ile Arg 340
1801    TTG GAT AAA AGC ATT AAA GAA GAT GTC CAG TTC GCT GAT TCA AGG ATT CGC

Pro Gln Thr Ile Ala Gly Glu Asp Thr Leu Asp Asp Met Gly Ile Phe Ser 357
1852    CCT CAA ACC ATT GCG GGT GAA GAC ACT TTG GAT GAC ATG GGG ATT TTC TCA

Ile Thr Ser Ser Asp Ser Gln Ala Met Gly Arg Val Gly Glu Val Ile Thr 374
1903    ATC ACT AGT TCT GAC TCT CAA GCG ATG GGC CGT GTG GGT GAA GTT ATC ACT

Arg Thr Trp Gln Thr Ala Asp Lys Asn Lys Lys Glu Phe Gly Arg Leu Lys 391
1954    AGA ACT TGG CAA ACA GCT GAC AAA AAT AAA AAA GAA TTT GGC CGC TTG AAA

Glu Glu Lys Gly Asp Asn Asp Asn Phe Arg Ile Lys Arg Tyr Leu Ser Lys 408
2005    GAA GAA AAA GGC GAT AAC GAC AAC TTC AGG ATC AAA CGC TAC TTG TCT AAA

Tyr Thr Ile Asn Pro Ala Ile Ala His Gly Ile Ser Glu Tyr Val Gly Ser 425
2056    TAC ACC ATT AAC CCA GCG ATC GCT CAT GGG ATT AGC GAG TAT GTC GGT TCT

Val Glu Val Gly Lys Val Ala Asp Leu Val Leu Trp Ser Pro Ala Phe Phe 442
2107    GTA GAA GTG GGC AAA GTG GCT GAC TTG GTA TTG TGG AGT CCC GCA TTC TTT

Gly Val Lys Pro Asn Met Ile Ile Lys Gly Gly Phe Ile Ala Leu Ser Gln 459
2158    GGT GTG AAA CCC AAC ATG ATC ATC AAA GGC GGG TTC ATC GCA TTG AGT CAA

Met Gly Asp Ala Asn Ala Ser Ile Pro Thr Pro Gln Pro Val Tyr Tyr Arg 476
2209    ATG GGT GAT GCG AAC GCT TCT ATC CCT ACC CCA CAA CCA GTT TAT TAC AGA

Glu Met Phe Ala His His Gly Lys Ala Lys Tyr Asp Ala Asn Ile Thr Phe 493
2260    GAA ATG TTC GCT CAT CAT GGT AAA GCT AAA TAC GAT GCA AAC ATC ACT TTT

Val Ser Gln Ala Ala Tyr Asp Lys Gly Ile Lys Glu Gly Leu Gly Leu Glu 510
2311    GTG TCT CAA GCG GCT TAT GAC AAA GGC ATT AAA GAA GGA TTA GGG CTT GAA
```

Fig. 3C

```
              Arg Gln Val Leu Pro Val Lys Asn Cys Arg Asn Ile Thr Lys Lys Asp Met  527
       2362   AGA CAA GTG TTG CCG GTA AAA AAT TGC AGA AAT ATC ACT AAA AAA GAC ATG

Gln Phe Asn Asp Thr Thr Ala His Ile Glu Val Asn Ser Glu Thr Tyr His  544
       2413   CAA TTC AAC GAC ACT ACC GCT CAC ATT GAA GTC AAT TCT GAA ACT TAC CAT

Val Phe Val Asp Gly Lys Glu Val Thr Ser Lys Pro Ala Asn Lys Val Ser  567
       2464   GTG TTC GTG GAT GGC AAA GAA GTA ACT TCT AAA CCA GCC AAT AAA GTG AGC

Leu Ala Gln Leu Phe Ser Ile Phe Stop              (BL2 primer)  576
       2515   TTG GCG CAA CTC TTT AGC ATT TTC TAG GATTTTTAGGAG CAACGCTTCCTTAAATCC
                  EcoRI
       2570   TGAATTCGAGCTCCGTCGACAAGCTTGCGGCCGCACTCGAGCACCACCACCACCACCACTGAGATCC
       2637   GGCTGCTAACAAAGCCCGAAAGGAAGCTGAGTTGGCTGCTGCCACCGCTGAGCAATAACTAGC ATAA
                             T7 terminator
       2704   CCCCTTGGGGCCTCTAAACGGGTCTTGAGGGGTTTTTTG
```

Fig. 3D

| GROUPS | #Swi.We | Route | Antigen | CT | Tx sche. |
|---|---|---|---|---|---|
| 1 | 10 | IN | 10ug rU +HCHO | No | 15 x 1d(d3-22) |
| 2 | 10 | IN | 10ug rU | No | 15 x 1d(d3-22) |
| 3 | 10 | IN | 10ug rU | 5 ug | 4 x 1w(d0,7, 14,21) |
| 4 | 10 | PO | 100ug rU +HCHO | No | 4 x 1w(d0,7, 14,21) |
| 5 | 10 | PO | 100ug rU | No | 4 x 1w(d0,7, 14,21) |
| 6 | 10 | PO | 25ug rU | 10ug | 4 x 1w(d0,7, 14,21) |
| 7 | 10 | untreated | | | |

BLOOD AND FECES COLLECTED ON DAY 32, AND SALIVA COLLECTED ON DAY 33. CHALLENGE ON DAY 36. SACRIFICE ON DAY 50.

W = WEEK; d = DAY

Fig. 7

IN/oral combination schedule of immunization

| Group | n | Schedule | Sacrifice |
|---|---|---|---|
| 1 | 10 | IN days 3-7; IG days 14 and 21 | 2 weeks |
| 2 | 10 | IN days 3-7; IG day 21 | 2 weeks |
| 3 | 10 | IN days 0,7; IG days 14, 21 | 2 weeks |
| 4 | 10 | IN + LT days 0, 7, 14, 21 (pos control) | 2 weeks |
| 5 | 10 | no treatment (neg control) | 2 weeks |
| 6 | 10 | IN days 3-7; IG days 14 and 21 | 10 weeks |
| 7 | 10 | IN + LT days 0, 7, 14, 21 | 10 weeks |
| 8 | 10 | oral + LT days 0, 7, 14, 21 (pos control) | 10 weeks |
| 9 | 10 | no treatment (neg control) | 10 weeks |

Urease dose: IN, 25 µg; IG 200µg
LT dose: IN, 2µg; IG 10µg
Challenge 2 weeks after immunization Assays:
urease
histology for gastritis, bugs, mast cells, eosinophils
Farside assay
anti-urease in serum, feces, saliva
ASCs in stomach sections

Fig. 9

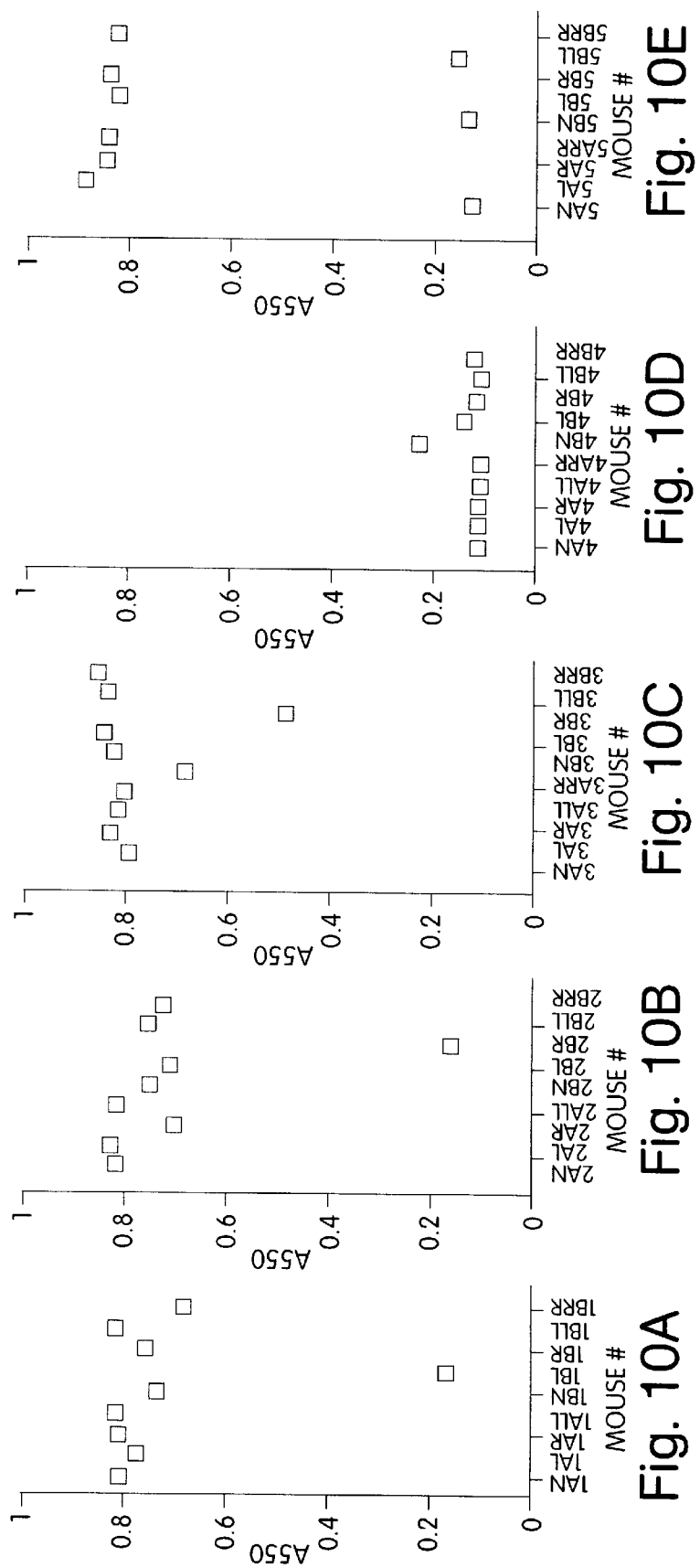

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 2735 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| TAATACGACT | CACTATAGGG | GAATTGTGAG | CGGATAACAA | TTCATCCACC | TTGATTGCGT | 60 |
| TATGTCTTCA | AGGAAAAACA | CTTTAAGAAT | AGGAGAATGA | GATGAAACTC | ACCCCAAAAG | 120 |
| AGTTAGATAA | GTTGATGCTC | CACTACGCTG | GAGAATTGGC | TAAAAACGC | AAAGAAAAG | 180 |
| GCATTAAGCT | TAACTATGTA | GAAGCAGTAG | CTTTGATTAG | TGCCCATATT | ATGGAAGAAG | 240 |
| CGAGAGCTGG | TAAAAAGACT | GCGGCTGAAT | TGATGCAAGA | AGGGCGCACT | CTTTTAAAAC | 300 |
| CAGATGATGT | GATGGATGGC | GTGGCAAGCA | TGATCCATGA | AGTGGGTATT | GAAGCGATGT | 360 |
| TTCCTGATGG | GACTAAACTC | GTAACCGTGC | ATACCCCTAT | TGAGGCCAAT | GGTAAATTAG | 420 |
| TTCCTGGTGA | GTTGTTCTTA | AAAAATGAAG | ACATCACTAT | CAACGAAGGC | AAAAAAGCCG | 480 |
| TTAGCGTGAA | AGTTAAAAAT | GTTGGCGACA | GACCGGTTCA | AATCGGCTCA | CACTTCCATT | 540 |
| TCTTTGAAGT | GAATAGATGC | CTAGACTTTG | ACAGAGAAAA | AACTTTCGGT | AAACGCTTAG | 600 |
| ACATTGCGAG | CGGGACAGCG | GTAAGATTTG | AGCCTGGCGA | AGAAAAATCC | GTAGAATTGA | 660 |
| TTGACATTGG | CGGTAACAGA | AGAATCTTTG | GATTTAACGC | ATTGGTTGAT | AGACAAGCAG | 720 |
| ACAACGAAAG | CAAAAAAATT | GCTTTACACA | GAGCTAAAGA | GCGTGGTTTT | CATGGCGCTA | 780 |
| AAAGCGATGA | CAACTATGTA | AAAACAATTA | AGGAGTAAGA | AATGAAAAG | ATTAGCAGAA | 840 |
| AAGAATATGT | TTCTATGTAT | GGTCCTACTA | CAGGCGATAA | AGTGAGATTG | GGCGATACAG | 900 |
| ACTTGATCGC | TGAAGTAGAA | CATGACTACA | CCATTTATGG | CGAAGAGCTT | AAATTCGGTG | 960 |
| GCGGTAAAAC | CCTAAGAGAA | GGCATGAGCC | AATCTAACAA | CCCTAGCAAA | GAAGAGTTGG | 1020 |
| ATTTAATTAT | CACTAACGCT | TTAATCGTGG | ATTACACCGG | TATTTATAAA | GCGGATATTG | 1080 |
| GTATTAAAGA | TGGCAAAATC | GCTGGCATTG | GTAAAGGCGG | TAACAAAGAC | ATGCAAGATG | 1140 |
| GCGTTAAAAA | CAATCTTAGC | GTAGGTCCTG | CTACTGAAGC | CTTAGCCGGT | GAAGGTTTGA | 1200 |
| TCGTAACGGC | TGGTGGTATT | GACACACACA | TCCACTTCAT | TTCACCCCAA | CAAATCCCTA | 1260 |
| CAGCTTTTGC | AAGCGGTGTA | ACAACCATGA | TTGGTGGTGG | AACCGGTCCT | GCTGATGGCA | 1320 |
| CTAATGCGAC | TACTATCACT | CCAGGCAGAA | GAAATTTAAA | ATGGATGCTC | AGAGCGGCTG | 1380 |
| AAGAATATTC | TATGAATTTA | GGTTTCTTGG | CTAAAGGTAA | CGCTTCTAAC | GATGCGAGCT | 1440 |
| TAGCCGATCA | AATTGAAGCC | GGTGCGATTG | GCTTTAAAAT | TCACGAAGAC | TGGGGCACCA | 1500 |
| CTCCTTCTGC | AATCAATCAT | GCGTTAGATG | TTGCGGACAA | ATACGATGTG | CAAGTCGCTA | 1560 |
| TCCACACAGA | CACTTTGAAT | GAAGCCGGTT | GTGTAGAAGA | CACTATGGCT | GCTATTGCTG | 1620 |
| GACGCACTAT | GCACACTTTC | CACACTGAAG | GCGCTGGCGG | CGGACACGCT | CCTGATATTA | 1680 |
| TTAAAGTAGC | CGGTGAACAC | AACATTCTTC | CCGCTTCCAC | TAACCCCACC | ATCCCTTTCA | 1740 |
| CCGTGAATAC | AGAAGCAGAG | CACATGGACA | TGCTTATGGT | GTGCCACCAC | TTGGATAAAA | 1800 |

| | | | | | |
|---|---|---|---|---|---|
| GCATTAAAGA | AGATGTTCAG | TTCGCTGATT | CAAGGATCCG | CCCTCAAACC | ATTGCGGCTG | 1860 |
| AAGACACTTT | GCATGACATG | GGGATTTTCT | CAATCACCAG | TTCTGACTCT | CAAGCGATGG | 1920 |
| GCCGTGTGGG | TGAAGTTATC | ACTAGAACTT | GGCAAACAGC | TGACAAAAAC | AAGAAAGAAT | 1980 |
| TTGGCCGCTT | GAAAGAAGAA | AAAGGCGATA | ACGACAACTT | CAGGATCAAA | CGCTACTTGT | 2040 |
| CTAAATACAC | CATTAACCCA | GCGATCGCTC | ATGGGATTAG | CGAGTATGTA | GGTTCAGTAG | 2100 |
| AAGTGGGCAA | AGTGGCTGAC | TTGGTATTGT | GGAGTCCAGC | ATTCTTTGGC | GTGAAACCCA | 2160 |
| ACATGATCAT | CAAAGGCGGA | TTCATTGCGT | TAAGCCAAAT | GGGCGATGCG | AACGCTTCTA | 2220 |
| TCCCTACCCC | ACAACCGGTT | TATTACAGAG | AAATGTTCGC | TCATCATGGT | AAAGCTAAAT | 2280 |
| ACGATGCAAA | CATCACTTTT | GTGTCTCAAG | CGGCTTATGA | CAAAGGCATT | AAAGAAGAAT | 2340 |
| TAGGACTTGA | AAGACAAGTG | TTGCCGGTAA | AAAATTGCAG | AAATATCACT | AAAAAAGACA | 2400 |
| TGCAATTCAA | CGACACTACT | GCTCACATTG | AAGTCAATCC | TGAAACTTAC | CATGTGTTCG | 2460 |
| TGGATGGCAA | AGAAGTAACT | TCTAAACCAG | CCAATAAAGT | GAGCTTGGCG | CAACTCTTTA | 2520 |
| GCATTTTCTA | GGATTTTTTA | GGAGCAACGC | TTCCTTAAAT | CCTGAATTCG | AGCTCCGTCG | 2580 |
| ACAAGCTTGC | GGCCGCACTC | GAGCACCACC | ACCACCACCA | CTGAGATCCG | GCTGCTAACA | 2640 |
| AAGCCCGAAA | GGAAGCTGAG | TTGGCTGCTG | CCACCGCTGA | GCAATAACTA | GCATAACCCC | 2700 |
| TTGGGGCCTC | TAAACGGGTC | TTGAGGGGTT | TTTTG | | | 2735 |

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Leu Thr Pro Lys Glu Leu Asp Lys Leu Met Leu His Tyr Ala
 1               5                  10                  15

Gly Glu Leu Ala Lys Lys Arg Lys Glu Lys Gly Ile Lys Leu Asn Tyr
             20                  25                  30

Val Glu Ala Val Ala Leu Ile Ser Ala His Ile Met Glu Glu Ala Arg
         35                  40                  45

Ala Gly Lys Lys Thr Ala Ala Glu Leu Met Gln Glu Gly Arg Thr Leu
     50                  55                  60

Leu Lys Pro Asp Asp Val Met Asp Gly Val Ala Ser Met Ile His Glu
 65                  70                  75                  80

Val Gly Ile Glu Ala Met Phe Pro Asp Gly Thr Lys Leu Val Thr Val
                 85                  90                  95

His Thr Pro Ile Glu Ala Asn Gly Lys Leu Val Pro Gly Glu Leu Phe
            100                 105                 110

Leu Lys Asn Glu Asp Ile Thr Ile Asn Glu Gly Lys Lys Ala Val Ser
        115                 120                 125

Val Lys Val Lys Asn Val Gly Asp Arg Pro Val Gln Ile Gly Ser His
    130                 135                 140

Phe His Phe Phe Glu Val Asn Arg Cys Leu Asp Phe Asp Arg Glu Lys
145                 150                 155                 160

Thr Phe Gly Lys Arg Leu Asp Ile Ala Ser Gly Thr Ala Val Arg Phe
                165                 170                 175

Glu Pro Gly Glu Glu Lys Ser Val Glu Leu Ile Asp Ile Gly Gly Asn
            180                 185                 190
```

```
        Arg  Arg  Ile  Phe  Gly  Phe  Asn  Ala  Leu  Val  Asp  Arg  Gln  Ala  Asp  Asn
                  195                      200                      205

Glu  Ser  Lys  Lys  Ile  Ala  Leu  His  Arg  Ala  Lys  Glu  Arg  Gly  Phe  His
             210                      215                      220

Gly  Ala  Lys  Ser  Asp  Asp  Asn  Tyr  Val  Lys  Thr  Ile  Lys  Glu
        225                      230                      235
```

( 2 ) INFORMATION FOR SEQ ID NO:3:

( i ) SEQUENCE CHARACTERISTICS:
        ( A ) LENGTH: 566 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
        Met  Lys  Lys  Ile  Ser  Arg  Lys  Glu  Tyr  Val  Ser  Met  Tyr  Gly  Pro  Thr
        1                   5                        10                       15

Thr  Gly  Asp  Lys  Val  Arg  Leu  Gly  Asp  Thr  Asp  Leu  Ile  Ala  Glu  Val
                       20                      25                       30

Glu  His  Asp  Tyr  Thr  Ile  Tyr  Gly  Glu  Glu  Leu  Lys  Phe  Gly  Gly  Gly
                  35                      40                       45

Lys  Thr  Leu  Arg  Glu  Gly  Met  Ser  Gln  Ser  Asn  Asn  Pro  Ser  Lys  Glu
             50                      55                       60

Glu  Leu  Asp  Leu  Ile  Ile  Thr  Asn  Ala  Leu  Ile  Val  Asp  Tyr  Thr  Gly
        65                       70                       75                       80

Ile  Tyr  Lys  Ala  Asp  Ile  Gly  Ile  Lys  Asp  Gly  Lys  Ile  Ala  Gly  Ile
                            85                      90                       95

Gly  Lys  Gly  Gly  Asn  Lys  Asp  Met  Gln  Asp  Gly  Val  Lys  Asn  Asn  Leu
                       100                     105                      110

Ser  Val  Gly  Pro  Ala  Thr  Glu  Ala  Leu  Ala  Gly  Glu  Gly  Leu  Ile  Val
                  115                     120                      125

Thr  Ala  Gly  Gly  Ile  Asp  Thr  His  Ile  His  Phe  Ile  Ser  Pro  Gln  Gln
             130                     135                      140

Ile  Pro  Thr  Ala  Phe  Ala  Ser  Gly  Val  Thr  Thr  Met  Ile  Gly  Gly  Gly
        145                     150                      155                      160

Thr  Gly  Pro  Ala  Asp  Gly  Thr  Asn  Ala  Thr  Thr  Ile  Thr  Pro  Gly  Arg
                            165                     170                      175

Arg  Asn  Leu  Lys  Trp  Met  Leu  Arg  Ala  Ala  Glu  Glu  Tyr  Ser  Met  Asn
                       180                     185                      190

Leu  Gly  Phe  Leu  Ala  Lys  Gly  Asn  Ala  Ser  Asn  Asp  Ala  Ser  Leu  Ala
                  195                     200                      205

Asp  Gln  Ile  Glu  Ala  Gly  Ala  Ile  Gly  Phe  Lys  Ile  His  Glu  Asp  Trp
             210                     215                      220

Gly  Thr  Thr  Pro  Ser  Ala  Ile  Asn  His  Ala  Leu  Asp  Val  Ala  Asp  Lys
        225                     230                      235                      240

Tyr  Asp  Val  Gln  Val  Ala  Ile  His  Thr  Asp  Thr  Leu  Asn  Glu  Ala  Gly
                            245                     250                      255

Cys  Val  Glu  Asp  Thr  Met  Ala  Ala  Ile  Ala  Gly  Arg  Thr  Met  His  Thr
                       260                     265                      270

Phe  His  Thr  Glu  Gly  Ala  Gly  Gly  Gly  His  Ala  Pro  Asp  Ile  Ile  Lys
                  275                     280                      285

Val  Ala  Gly  Glu  His  Asn  Ile  Leu  Pro  Ala  Ser  Thr  Asn  Pro  Thr  Ile
             290                     295                      300

Pro  Phe  Thr  Val  Asn  Thr  Glu  Ala  Glu  His  Met  Asp  Met  Leu  Met  Val
        305                     310                      315                      320
```

| | | | | | | | | | | | | | | |
|---|---|---|---|---|---|---|---|---|---|---|---|---|---|---|
| Cys | His | His | Leu | Asp 325 | Lys | Ser | Ile | Lys | Glu 330 | Asp | Val | Gln | Phe | Ala Asp 335 |
| Ser | Arg | Ile | Arg 340 | Pro | Gln | Thr | Ile | Ala 345 | Ala | Glu | Asp | Thr | Leu 350 | His Asp |
| Met | Gly | Ile 355 | Phe | Ser | Ile | Thr | Ser 360 | Ser | Asp | Ser | Gln | Ala 365 | Met | Gly Arg |
| Val | Gly 370 | Glu | Val | Ile | Thr | Arg 375 | Thr | Trp | Gln | Thr | Ala 380 | Asp | Lys | Asn Lys |
| Lys 385 | Glu | Phe | Gly | Arg | Leu 390 | Lys | Glu | Glu | Lys | Gly 395 | Asp | Asn | Asp | Asn Phe 400 |
| Arg | Ile | Lys | Arg | Tyr 405 | Leu | Ser | Lys | Tyr | Thr 410 | Ile | Asn | Pro | Ala | Ile Ala 415 |
| His | Gly | Ile | Ser 420 | Glu | Tyr | Val | Gly | Ser 425 | Val | Glu | Val | Gly | Lys 430 | Val Ala |
| Asp | Leu | Val 435 | Leu | Trp | Ser | Pro | Ala 440 | Phe | Phe | Gly | Val | Lys 445 | Pro | Asn Met |
| Ile | Ile 450 | Lys | Gly | Gly | Phe | Ile 455 | Ala | Leu | Ser | Gln | Met 460 | Gly | Asp | Ala Asn |
| Ala 465 | Ser | Ile | Pro | Thr | Pro 470 | Gln | Pro | Val | Tyr | Tyr 475 | Arg | Glu | Met | Phe Ala 480 |
| His | His | Gly | Lys | Ala 485 | Lys | Tyr | Asp | Ala | Asn 490 | Ile | Thr | Phe | Val | Ser Gln 495 |
| Ala | Ala | Tyr | Asp 500 | Lys | Gly | Ile | Lys | Glu 505 | Glu | Leu | Gly | Leu | Glu 510 | Arg Gln |
| Val | Leu | Pro 515 | Val | Lys | Asn | Cys | Arg 520 | Asn | Ile | Thr | Lys | Lys 525 | Asp | Met Gln |
| Phe | Asn 530 | Asp | Thr | Thr | Ala | His 535 | Ile | Glu | Val | Asn | Pro 540 | Glu | Thr | Tyr His |
| Val 545 | Phe | Val | Asp | Gly | Lys 550 | Glu | Val | Thr | Ser | Lys 555 | Pro | Ala | Asn | Lys Val 560 |
| Ser | Leu | Ala | Gln | Leu 565 | Phe | | | | | | | | | |

MULTIMERIC, RECOMBINANT UREASE VACCINE

This is a continuation of application Ser. No. 08/431,041, filed Apr. 28, 1995, now abandoned.

BACKGROUND OF THE INVENTION

This invention relates to methods and immunogenic compositions (e.g., vaccines) for preventing and treating Helicobacter infection.

Helicobacter is a genus of spiral, gram-negative bacteria which colonize the gastrointestinal tracts of mammals. Several species colonize the stomach, most notably *Helicobacter pylori*, *Helicobacter heilmanii*, *Helicobacter fells*, and *Helicobacter mustelae*. *H. pylori* is the species most commonly associated with human infection. *H. heilmanii* is also associated with human infection, but at a lower frequency than *H. pylori*.

Helicobacter infects over 50% of adult populations in developed countries, and nearly 100% in developing countries and some Pacific rim countries, making it one of the most prevalent infections of humans worldwide. Infection with *H. pylori* results in chronic stomach inflammation in all infected subjects, although the clinical gastroduodenal diseases associated with Helicobacter generally appear from several years to several decades after the initial infection. *H. pylori* is the causative agent of most peptic ulcers and chronic superficial (type B) gastritis. *H. pylori* infection is also associated with atrophy of the gastric mucosa, gastric adenocarcinoma, and non-Hodgkin's lymphoma of the stomach. The role of *H. pylori* in these diseases has been summarized in numerous reviews (Blaser, *J. Infect. Dis.* 161:626–633, 1990; Scolnick et al., *Infect. Agents Dis.* 1:294–309, 1993; Goodwin et al., "*Helicobacter pylori*," *Biology and Clinical Practice*, CRC Press, Boca Raton, Fla., 465 pp, 1993; Northfield et al., "*Helicobacter pylori*," Infection, Kluwer Acad. Pub., Dordrecht, 178 pp, 1994).

Helicobacter colonizes the stomach mucus gel and the underlying gastric epithelial cells. Normally, the low pH of the stomach provides a chemical barrier to infectious agents. Helicobacter successfully breaches this barrier by producing urease, an enzyme present on the bacterial cell surface. Urease catalyzes the hydrolysis of urea to produce ammonium hydroxide, which provides a buffering cloud of ammonia around the bacterium, allowing it to withstand the low pH environment of the stomach and establish infection (Ferrero et al., *Microb. Ecol. Hlth. Dis.* 4:121–134, 1991). The structural genes encoding H. pylori urease, ureA and ureB, have been cloned and sequenced (Clayton et al., *Nucl. Acids. Res.* 18:362, 1990; Labigne et al., *J. Bacteriol.* 173:1920–1931, 1991), and a recombinant *H. pylori* urease has been purified (Hu et al., *Infect. Immun.* 60:2657–2666, 1992).

If untreated, *H. pylori* infection and the associated gastritis persist lifelong, despite the host's systemic and local immune responses to the bacterium (Crabtree et al., "Host responses," in Northfield TC et al. (Eds.), *Helicobacter pylori Infection*, Kluwer Acad. Pub., Dordrecht, pp. 40–52, 1991; Kist "Immunology of Helicobacter pylori," in *Helicobacter pylori in peptic ulceration and gastritis*. Marshall et al., Eds., Blackwell Sci. Pub., Oxford, pp. 92–110, 1991; Fox et al., *Infect. Immun.* 61:2309–2315, 1993). Conventional treatment of peptic ulcer disease associated with *H. pylori* infection involves the use of one or more antibiotics combined with a proton pump inhibitor or an $H_2$-receptor antagonist. Such treatment regimens are unsuccessful in 10% to 70% of patients. Moreover, successful eradication of *H. pylori* infection with antibiotics does not prevent subsequent reinfection. The most effective conventional treatment is a triple therapy with bismuth, metronidazole, and either amoxicillin or tetracycline. The triple therapy is complicated by a complex and prolonged dosing regimen, a high incidence of side-effects, poor compliance, and emergence of resistant bacterial strains (Hentschel et al., *N. Engl. J. Med.* 328:308–312, 1993).

There is a clear need for prophylactic and therapeutic regimens for Helicobacter infection which are simple to administer, well-tolerated, and result in long-lasting immunity against infection and/or reinfection.

SUMMARY OF THE INVENTION

We have shown that vaccine compositions containing multimeric, recombinant *Helicobacter pylori* urease are effective for preventing and treating Helicobacter infection.

Accordingly, in a first aspect, the invention features a vaccine for inducing a protective or therapeutically effective mucosal immune response to Helicobacter infection in a patient (e.g., a human patient). The vaccine of the invention contains a plurality of multimeric complexes (e.g., octamers, hexamers, or tetramers) of recombinant, enzymatically inactive urease 25 (e.g., *H. pylori* urease) in a pharmaceutically acceptable carrier substance (e.g., sterile water or 2% weight/volume sucrose). In a preferred embodiment, the multimeric complexes of recombinant, enzymatically inactive urease may be freeze-dried prior to administration.

In a first embodiment, the vaccine contains multimeric complexes containing eight Urease A subunits and eight Urease B subunits, multimeric complexes comprising six Urease A subunits and six Urease B subunits, or multimeric complexes comprising four Urease A subunits and four Urease B subunits.

In a second embodiment, the vaccine contains multimeric complexes containing eight Urease A subunits and eight Urease B subunits (octomer), multimeric complexes comprising six Urease A subunits and six Urease B subunits (hexamer), and multimeric complexes comprising four Urease A subunits and four Urease B subunits (tetramer).

The vaccine may be administered to a mucosal surface, e.g., a nasal or oral surface. The vaccine may be administered with gastric neutralization using, e.g., sodium bicarbonate, or without gastric neutralization. In a preferred embodiment, oral administration is carried out without gastric neutralization.

In addition to the multimeric complexes of recombinant, enzymatically inactive Helicobacter urease, the vaccine may contain a mucosal adjuvant, e.g., an adjuvant derived from the heat-labile enterotoxin of enterotoxigenic *Escherichia coli*, or derived from cholera toxin. Fragments, mutants, or analogs of adjuvants that maintain adjuvant activity may be used in vaccine of the invention.

In a second aspect, the invention features methods of preventing or treating Helicobacter infection in a patient. In these methods, an immunogenically effective amount of a composition containing a plurality of multimeric complexes of recombinant, enzymatically inactive Helicobacter (e.g., *Helicobacter pylori*) urease is administered to a mucosal surface (e.g., an intranasal or oral surface) of the patient. An advantage to intranasal delivery is that less antigen and adjuvant are required in order to produce a protective or therapeutic immune response.

In a first embodiment, the composition contains multimeric complexes comprising eight Urease A subunits and eight Urease B subunits, multimeric complexes comprising six Urease A subunits and six Urease B subunits, or multimeric complexes comprising four Urease A subunits and four Urease B subunits.

In a second embodiment, the composition contains multimeric complexes comprising eight Urease A subunits and eight Urease B subunits, multimeric complexes comprising six Urease A subunits and six Urease B subunits, and multimeric complexes comprising four Urease A subunits and four Urease B subunits.

The composition may be administered with gastric neutralization using, e.g., sodium bicarbonate, or without gastric neutralization. In a preferred embodiment, oral administration is carried out without gastric neutralization.

In a preferred embodiment, the composition is administered in association with a mucosal adjuvant, e.g., an adjuvant derived from heat-labile enterotoxin of enterotoxigenic *Escherichia coli* or cholera toxin.

In a further preferred embodiment, the multimeric complexes of recombinant, , enzymatically inactive Helicobacter (e.g., *Helicobacter pylori*) urease is freeze-dried prior to administration.

By "vaccine" is meant a composition containing at least one antigen which, when administered to a patient, elicits or enhances an immune response to the antigen that is effective in the prevention of disease, or in the treatment of disease associated with a pre-existing infection.

By "immunogenically effective amount" is meant an amount of a composition that is effective in eliciting an immune response (e.g., a humoral or a mucosal immune response) when administered to a patient (e.g., human patient).

By "therapeutically effective immune response" is meant an immune response which is effective in treating a preexisting disease, particularly a preexisting bacterial infection.

By "Helicobacter" is meant any bacterium of the species Helicobacter, particularly a *Helicobacter bacterium* which infects humans (e.g., *H. pylori*).

By "urease" is meant an enzyme (e.g., *H. pylori* urease) which catalyzes the conversion of urea into ammonium hydroxide and carbon dioxide. Urease activity thereby causes an increase in the pH of the medium or other environment in which the enzyme is located.

By "multimeric complex" is meant a macromolecular complex composed of polypeptides (e.g., urease polypeptides). The polypeptides may be associated in the complex by a variety of intermolecular interactions, such as covalent bonds (e.g., disulfide bonds), hydrogen bonds, and ionic bonds.

By "buffer free" or "free of buffer" is meant that the composition contains no compounds which effect a significant increase in pH, and/or is not administered to a patient in conjunction with any such pH-raising compound. "pH-raising buffer compounds," as meant herein, particularly refers to those compounds which effect an increase in stomach acid pH following oral administration to a human patient.

By "mucosal adjuvant" is meant a compound (e.g., an immunomodulator) which non-specifically stimulates or enhances a mucosal immune response (e.g., production of IgA antibodies). Administration of a mucosal adjuvant in conjunction with an immunogenic composition facilitates the induction of a mucosal immune response to the immunogenic compound.

Other features and advantages of the invention will be apparent from the following description of the preferred embodiments thereof, and from the claims.

DETAILED DESCRIPTION

The drawings are first described.

Drawings

FIG. 1 is a diagram showing the restriction enzyme map of the 2.5 kb PCR product cloned from pSCP1. The numbers above the map indicate nucleotide positions using the first base pair (bp) of BL1 as nucleotide #1. Locations of ureA and ureB genes and the direction of transcription of these genes are shown. The locations of restriction enzyme cleavage sites are shown below the genes. The numbers next to the name of each restriction enzyme indicate the locations of the first base pair in the recognition sequence for the enzyme indicated.

FIG. 2 is a diagram of the genetic map of the expression plasmid pORV214. The ureA and ureB genes are shown as open bars with arrows. The solid arrow and solid bar represent the T7 promoter and terminator sequences, respectively. Thin lines represent pBR322 DNA. The phage and plasmid origins of replication on the plasmid are shown by large shaded arrows, denoted "f1 origin" and "ori," respectively, and indicate the direction of DNA synthesis. The genes encoding kanamycin resistance (kan) and the lactose repressor (lacI) are shown as shaded bars. The BamHI and EcoRI sites used for cloning the PCR product are indicated. Arrows within bars representing lacI, ureA, ureB, and kan genes indicate the direction of transcription.

FIG. 3 is a schematic representation of the nucleotide sequence of the *H. pylori* locus encoding the ureA and ureB genes, as well as the transcriptional regulatory sequences from pORV214 (SEQ ID NO: 1). The start codons and predicted amino acid sequences of ureA (SEQ ID NO: 2) and ureB (SEQ ID NO: 3) are shown above the DNA sequence. Numbers to the left of the sequence correspond to nucleotides and those on the right indicate amino acid positions. The sequences corresponding to the PCR primers are underlined and the BamHI and EcoRI sites used to clone the product are indicated. The predicted transcriptional initiation site (G) and direction of transcription are shown with an arrow. The ribosomal binding site (RBS) is indicated. The sequences which regulate transcriptional initiation (T7 promoter and lac operator) and termination are underlined and labeled.

FIG. 7 is a table showing the experimental protocol used for comparing intranasal and oral immunization routes for recombinant urease.

FIG. 9 is a table showing the experimental protocol used for comparing intranasal and intragastric immunization routes for recombinant urease.

FIG. 10 is a series of graphs showing the results of urease tests carried out on the mice treated according to the protocol illustrated in FIG. 9.

CLONING OF THE UREA AND UREB GENES

The structural genes encoding urease, ureA, and ureB, have been cloned (Clayton et al., Nucl. Acids. Res. 18:362, 1990; Labigne et al., J. Bacteriol. 173:1920–1931, 1991), and the recombinant urease encoded by these genes has been purified (Hu et al., Infect. Immun. 60:2657–2666, 1992). For use in the present invention, urease was cloned from a clinical isolate of H. pylori (CPM630) obtained from a clinical specimen provided by Dr. Tabaqchali, St. Bartholomew's Medical College, University of London. A genomic DNA library of strain CPM630 was prepared in the lambda phage vector EMBL3. Plaques were screened for reactivity with rabbit anti-Helicobacter urease polyclonal antibody, and a single reactive plaque was isolated. This clone contained a 17 kb SalI fragment that encoded the ureA and ureB genes. The 17 kb fragment was subcloned onto pUC18 and designated pSCP1. A 2.7 kb TaqI fragment was subcloned (pTCP3) and completely sequenced. The 2.7 kb TaqI fragment encoded both ureA and ureB.

Figure 1:
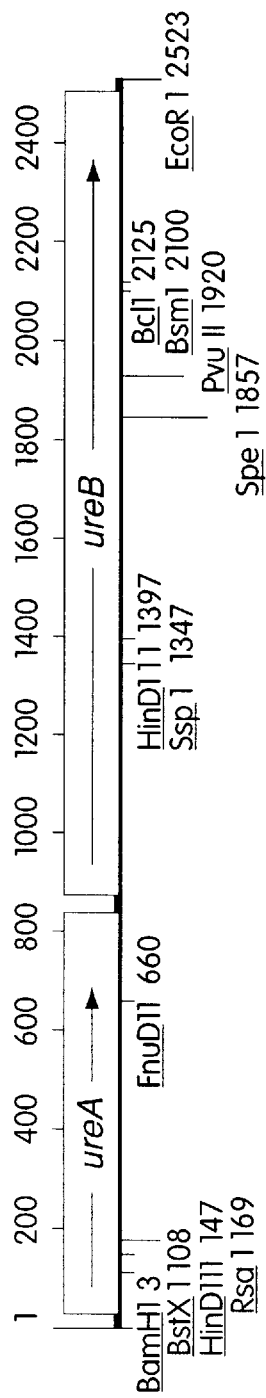

The primers BL1 (CGG GAT CCA CCT TGA TTG CGT TAT GTC T; SEQ ID NO: 4) and BL2 (CGG AAT TCA GGA TTT AAG GAA GCG TTG; SEQ ID NO: 5) were used to amplify and clone a 2.5 kb fragment from pSCP1. BL1 and BL2 correspond to nucleotides 2605–2624 of GenBank accession number M60398 (the BL1 primer) and nucleotides 2516–24998 of EMBL accession number X17079 (the BL2 primer). A restriction enzyme map of the 2.5 kb fragment PCR product is shown in FIG. 1. The 2.5 kb fragment contains the entire coding region of ureA and ureB, as well as translational start signals from H. pylori upstream of ureA.

Expression of recombinant urease

Figure 2:
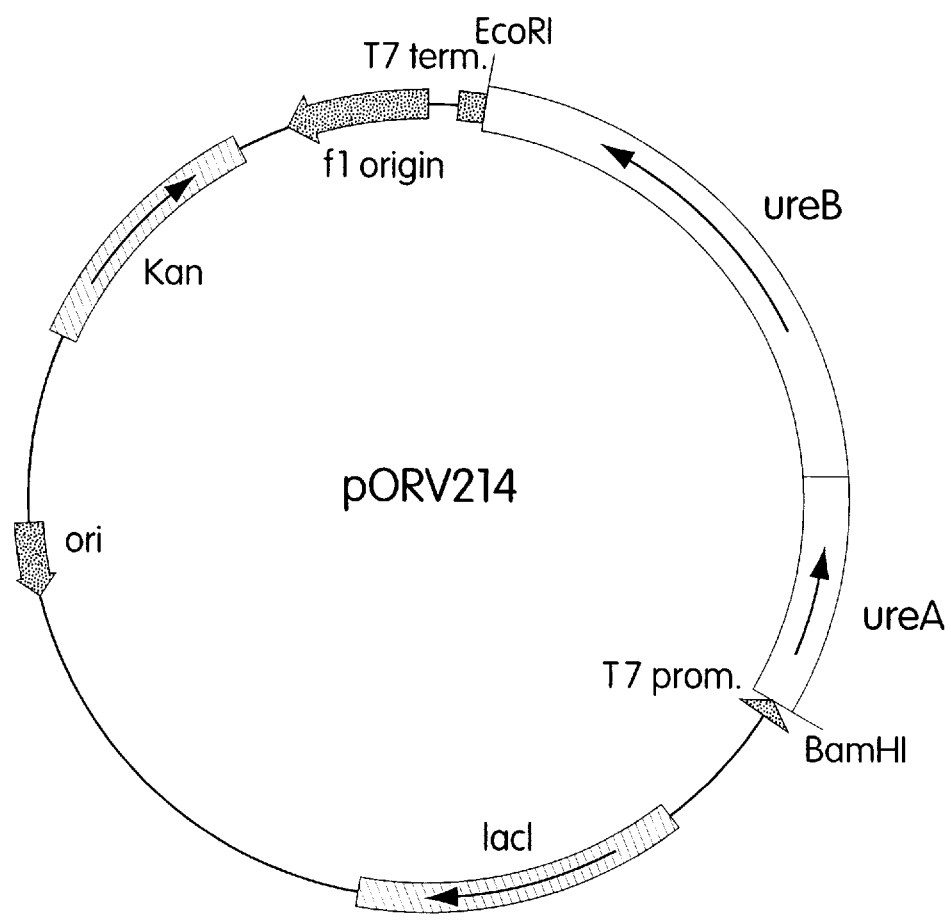

The purified 2.5 kb PCR fragment containing the genes encoding ureA and ureB was digested with EcoRI and BamHI and inserted into the expression vector pET24+ (Novagen) to produce the plasmid pORV214 (FIG. 2). pET24+ contains the colE1 origin of replication, the filamentous phage (f1) origin of replication for single strand rescue, and the kanamycin resistance gene of Tn903. The fragment was inserted downstream of the T7 promoter, which provides transcription initiation for the urease genes. Lactose operator (lacO) sequences are present between the T7 promoter and the cloning sites to provide inducible expression of the urease genes. A T7 transcription terminator sequence is located downstream of the cloning sites. The vector also contains the lactose repressor gene (lacI) to ensure complete repression of expression. Other sequences present in the vector are derived from pBR322, which served as the backbone for vector construction.

The initial ligation mixture, containing the 2.5 kb PCR EcoRI-BamHI fragment and the pET24+ vector digested with EcoRI and BamHI, was used to transform XL1-Blue (Stratagene, La Jolla, Calif.) prepared by the $CaCl_2$ method. XL1-Blue is an E. coli strain that does not express T7 RNA polymerase. Kanamycin resistant colonies were directly screened by PCR using urease specific primers. Plasmid DNA from several positive colonies was extracted using Qiagen minispin columns (Qiagen, Chatsworth, Calif.) and checked for the correct restriction digestion pattern.

Purified pORV214 DNA was used to transform the E. coli strain BL21-DE3 (Novagen) prepared by the $CaCl_2$ method. BL21-DE3 is an E. coli B strain that is lysogenized with lambda phage DE3, a recombinant phage that encodes T7 RNA polymerase under the control of the lavUV5 promoter. BL21 is deficient in ion and ompT proteases, as well as the $hsdS_B$ restriction/modification system and dcm DNA methylation. DNA was prepared from kanamycin resistant colonies with Qiagen mini spin columns and screened by restriction enzyme analysis using BamHI and EcoRI to confirm the presence of the plasmid. Urease expression was assessed by examination of BL21-DE3 (pORV214) cell lysates by SDS-PAGE and Western blot. Several positive clones had the correct restriction endonuclease digestion pattern and expressed urease.

A single clone containing pORV214 was selected, grown on LB plates containing kanamycin (50 μg/ml), harvested, and stored at −80° C. in LB containing 50% glycerol. A research cell bank was prepared by growing a sample from the glycerol stock on LB plates containing kanamycin, selecting an isolated colony, and inoculating a LB broth culture containing kanamycin. This culture was grown to $OD_{600}$ of 1.0, pelleted, and resuspended in an equal volume of LB containing 50% glycerol. These research cell bank (RCB) aliquots (100 μl) were then stored at −80° C. A master cell bank (MCB) was similarly prepared using an isolated colony from the research cell bank, and a manufacturer's working cell bank (MWCB) was prepared using an isolated colony from the MCB.

The MCB and MWCB cells were viable, kanamycin resistant, and displayed a normal E. coli colony morphology. T7 RNA polymerase expression and lambda phage lysogeny was confirmed using appropriate tests, which are well known in the art. Urease expression was IPTG-inducible in the MCB and MWCB cells, as determined by examination of cultures grown in the presence of IPTG, and analysis of lysates from these cell cultures on SDS-PAGE. Production of 60 kDa and 29 kDa proteins (UreB and UreA, respectively) by the MCB and MWCB cells increased with the incubation time.

Plasmid DNA was isolated from the MCB and MWCB cells and was tested by restriction enzyme analysis, restriction fragment length polymorphism (RFLP), and DNA sequence analysis to confirm plasmid structure. The MCB harbored a plasmid with the appropriate restriction endonuclease digestion pattern with no deletions or rearrangements of the plasmid. Likewise, there were no differences between the RFLP fingerprint of pSCP1 and the RFLP fingerprints of plasmid DNA from MCB and MWCB, indicating that the urease genes had not undergone detectable (>50 bp) deletions or rearrangements in the cloning process or in the manufacture of the cell banks.

The coding regions of ureA and ureB, and the sequences of the promoter and termination regions of the plasmid isolated from MCB cells was sequenced. Sequencing reactions were performed using the Di-Deoxy Cycle Sequencing Kit, according to the manufacturer's instructions (Applied Biosystems, Inc., Foster City, Calif.) using fluorescent-labeled dideoxynucleotides. The sequences of the ureA and ureB genes, with predicted protein sequences, as well as the DNA sequences of flanking regions are shown in FIG. 3.

Large-scale production of recombinant urease

The fermentor(s) to be used was cleaned and sterilized according to approved procedures. The culture medium contained 24 g/L yeast extract, 12 g/L tryptone, 6–15 g/L glycerol, in RO/DI water. Since pORV214 was sufficiently stable in the absence of antibiotics, no antibiotics were present in the large-scale fermentation cultures. Antifoam was added and the unit was sterilized in place.

For production in the 40 liter fermentor, a vial of the MWCB was thawed and used to inoculate a four liter shaker flask containing one liter of LB broth (1% tryptone, 0.5% yeast extract, 1% NaCl) without antibiotics. The culture was shaken at 37° C. for 16–24 hours. The inoculum is then transferred to the 40 liter fermentor (30 liter working volume) containing the production media described above. Fermentation was carried out with aeration and agitation until the cell density determined by $OD_{600}$ was approximately 8–10. The inducer isopropyl B-D-thiogalactopyranoside (IPTG) was then added to a final concentration of 0.1 mM. Induction was allowed to proceed for 16–24 hours. The cells were harvested by centrifugation and the wet paste was aliquoted into polypropylene storage containers and stored at −80° C. For production at the 400 liter scale (300 liter working volume), the inoculum and culture in the 40 liter vessel were prepared as described above. When the 40 liter vessel reached an $OD_{600}$ of approximately 5.0, it was used to inoculate the 400 liter fermentor. The culture was further incubated to an $OD_{600}$ of 8–10. The culture was then induced, harvested, and stored, as described above. This procedure required 2–3 generations more than the 40 liter process.

Purification of recombinant H. pylori urease

Containers of cell paste produced by the fermentation processes described above were removed from storage, thawed at room temperature, and re-suspended in 20 mM sodium phosphate/1 mM EDTA buffer, pH 6.8. The resuspended cells were disrupted by extrusion through a narrow orifice under pressure (Microfluidizer Cell Disruptor). Disrupted cells were centrifuged at 4° C. to sediment cell debris and the supernatant containing soluble urease was collected.

A solution of 3M sodium chloride was added to the cell supernatant to a final concentration of 0.1M. The supernatant was then applied to a DEAE-Sepharose column equilibrated in 20 mM sodium phosphate/1 mM EDTA, and the pass-through was collected for further processing. The pass-through was diafiltered into 20 mM sodium phosphate/1 mM EDTA, pH 6.8, with a 100 kDa cutoff membrane to remove low molecular weight contaminants and to reduce ionic strength.

This material was applied to a second DEAE-Sepharose column equilibrated in 20 mM sodium phosphate/1 mM EDTA. The pass-through was discarded and the column rinsed with 20 mM sodium phosphate/1 mM EDTA, pH 6.8. The bound material was eluted with approximately three column volumes of 0.1M NaCl/1 mM 2-mercaptoethanol. Effective elution of the bound urease was controlled by the volume and flow rate of the elution buffer.

The partially purified urease was diafiltered against 25 mM Tris-HCl, pH 8.6, and applied to a Q-Sepharose column. The column was washed with approximately two column volumes of the same buffer and the pass-through containing highly purified urease was collected.

The pass-through from the Q-Sepharose step was then concentrated and diafiltered into 2% sucrose in water for injection (WFI), pH 7.5.

Characterization of the antigenicity and subunit composition of Purified recombinant H. pylori urease To compare the antigenicity and subunit composition of recombinant H. pylori urease to native H. pylori urease, native H. pylori urease was purified and used as an antigen to produce polyclonal anti-urease antibodies, as well as mono-specific polyclonal anti-UreA, anti-UreB, and anti-urease holoenzyme antibodies.

Native H. pylori urease was purified using a modification of the procedure reported by Hu and Mobley (Infect. Immun. 58:992–998, 1990). H. pylori strain ATCC 43504 (American Type Culture Collection, Rockville, Md.) was grown on Mueller-Hinton agar (Difco Laboratories, Detroit, Mich.) containing 5% sheep red blood cells (Crane Labs, Syracuse, N.Y.) and antibiotics (5 µg/ml trimethoprim, 10 µg/ml vancomycin and 10 U/ml polymyxin B sulfate) (TVP, Sigma Chemical Co., St. Louis, Mo.). Plates were incubated 3–4 days at 37° C. in 7% $CO_2$ and 90% humidity, and bacteria were harvested by centrifugation. The bacteria were suspended in water or 20 mM phosphate, 1 mM EDTA, 1 mM β-mercaptoethanol (pH 6.8) containing protease inhibitors, lysed by sonication and clarified by centrifugation. The clarified supernatant was mixed with 3M sodium chloride to a final sodium chloride concentration of 0.15M and passed through DEAE-Sepharose (Fast Flow). Active urease that passed through the column was collected, concentrated in a Filtron Macrosep 100 centrifugal filtration unit, and then passed through a Superose-12 or Superdex 200 size exclusion column. Size-exclusion chromatography was performed using Pharmacia FPLC prepacked columns. The fractions containing urease activity were pooled, concentrated, and further purified by FPLC anion-exchange chromatography on a Mono-Q sepharose column prepacked by Pharmacia. The bound urease was eluted using a sodium chloride gradient. The fractions with urease activity were pooled and concentrated using Macrosep 100 centrifugal filters from Filtron Inc. For some lots, a final purification was achieved by analytical size-exclusion FPLC on Superose-12 columns.

Polyclonal antiserum to H. pylori urease was produced by immunizing three female New Zealand white rabbits with purified native H. pylori urease. The animals were pre-bled to confirm non-immune status and then immunized subcutaneously with 150 µg urease in complete Freund's adjuvant. Two booster doses of 150 µg each were administered subcutaneously 27 and 45 days later with Freund's incomplete adjuvant. After confirmation of the immune response by ELISA and Western blotting against purified urease, the animals were exsanguinated. The blood was clotted at 4° C. overnight and serum was harvested by centrifugation. Serum IgG was purified by ammonium sulfate precipitation (50%) overnight at 4° C. The precipitate was resuspended in PBS and dialyzed to remove ammonium sulfate. The anti-urease titer of the IgG from each animal was found to be $1:10^7$ and the antibodies from the three animals were pooled. The protein concentration was determined to be 17.3 mg/ml. Aliquots of 0.2 ml each were prepared and stored at −80° C.

Mouse polyclonal ascites against H. pylori urease holoenzyme ("MPA3") was prepared by injecting five mice subcutaneously with 10 µg native urease holoenzyme in complete Freund's adjuvant on Day 0. The mice were boosted on Days 10 and 17, bled on day 24 to confirm anti-urease immune response, and boosted again on Day 26. On Day 28 the mice were injected intraperitoneally with Sarcoma 180 cells. A final intraperitoneal booster dose of 10 µg urease was given on Day 31, and ascitic fluids collected seven days later.

The ascitic fluids were incubated for two hours at room temperature and then at 4° C. for 16 hours; clots were disrupted by vortexing and removed by centrifugation at 10,000 rpm for 10 minutes. After overnight incubation at 4° C. in plastic tubes, the fluids formed solid clots. These were homogenized, diluted five-fold with PBS, and reclarified by centrifugation at 10,000 rpm for 10 minutes. Thirty-six ml of diluted ascitic fluids were collected and frozen at −20° C. in 300 µl aliquots. Western blot analyses confirmed that the antibody reacts with UreA and UreB subunits. An endpoint titer of 1:300,000 was achieved in ELISA against urease.

Mouse polyclonal ascites against *H. pylori* UreA ("MPA4") was prepared by injecting mice subcutaneously with native UreA subunit *H. pylori* urease isolated by electroelution from SDS-PAGE gels. Subsequent steps in the preparation of anti-ureA ascites were performed as described above for generation of antibodies against the holoenzyme.

Mouse polyclonal ascites against native *H. pylori* UreB subunit ("MPA6") was prepared by injecting mice subcutaneously with native UreB isolated by electroelution from SDS-PAGE gels. Subsequent steps in the preparation of anti-UreB ascites were performed as described above for generation of antibodies against the holoenzyme.

MAB71 is an IgA monoclonal antibody against *H. felis* urease which recognizes a protective epitope on the B subunit. Preparation of this antibody is described in Czinn et al., *J. Vaccine* 11(6):637–642, 1993.

The antibodies described above were used in Western blot experiments to characterize the purified recombinant *H. pylori* urease.

SDS-PAGE and Western blot analysis of recombinant urease

Recombinant urease was first analyzed by SDS-PAGE (12.5%) run under reducing conditions. Two major protein bands (29 kDa and 60 kDa) and several lighter bands (approximately 38 kDa) were evident. To identify the proteins in these bands, Western blots were performed using the anti-urease and anti-urease subunit antibodies described above. The 60 kDa protein reacted with MPA3 (anti-urease holoenzyme) and MPA6 (anti-UreB), but not with MPA4 (anti-UreA). The 29 kDa protein reacted with MPA3 (anti-urease holoenzyme) and MPA3 (anti-UreA), but not with MPA6 (anti-UreB). The lighter 38 kDa band reacted with MPA3 anti-urease holoenzyme) and MPA6 (anti-UreB), indicating that this protein is a portion of UreB.

Two faint high molecular weight (>150 kDa) bands were evident in SDS-PAGE gels. Both bands reacted faintly with antibodies to both UreA and UreB, indicating that a minor portion of recombinant urease subunits form covalent units resistant to sulfhydryl reduction under the conditions used. No other protein bands were apparent in Coomassie-stained gels. Hence, all proteins detected in the purified product are either UreA, UreB, or a derivative of UreA or UreB.

The wet Coomassie-stained SDS-PAGE gel was scanned using an Ultroscan XL laser densitometer and a Gel Scan XL software program (Pharmacia-LKB Biotechnology, Piscataway, N.J.). The densitometry data were consistent with a 1:1 molar ratio of the UreA:UreB subunits, as expected from the structure of native *H. pylori* urease. UreA and UreB accounted for more than 95% of the total protein present in the purified urease preparation. The estimated average value for the combined UreA+UreB peaks was 95.2% ±1.2%.

Analytical size-exclusion HPLC of purified recombinant urease

The purity and molecular composition of purified recombinant urease was determined by analytical size-exclusion high performance liquid chromatography. Chromatography was performed using a Beckman System Gold HPLC consisting of Pump 126, diode array dual wavelength detector 168, System Gold Software Version V7.11, Progel-TSK G4000SWXL (5 mm×30 cm i.d) column, and SWXL guard column from SupelCo. Chromatography was performed under isocratic conditions using 100 mM phosphate, 100 mM sodium chloride buffer, pH 7.0. The column was calibrated using molecular weight markers from Pharmacia-LKB.

Figure 4:
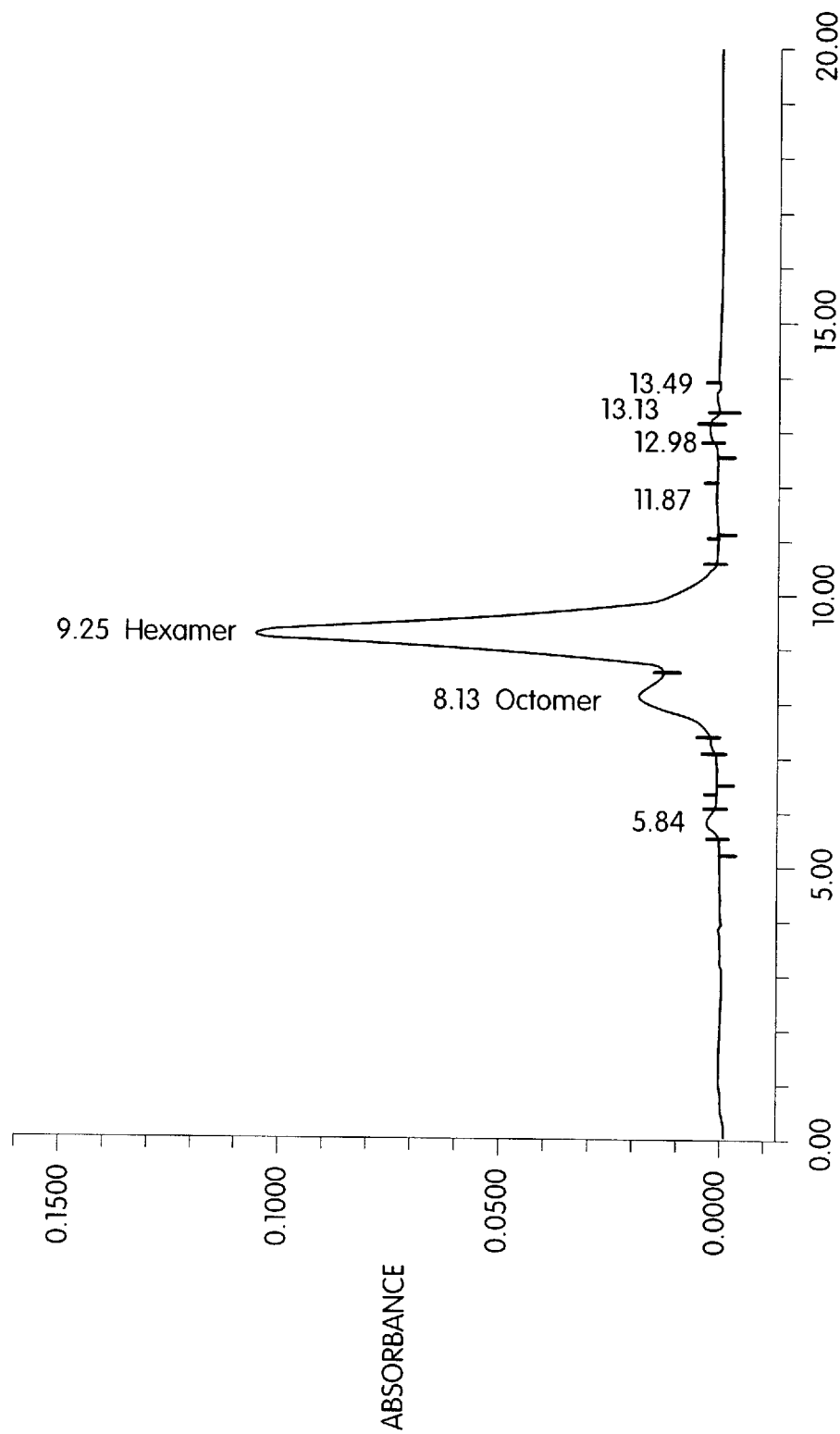
FIG. 4 is a graph showing analytical size exclusion HPLC for recombinant urease.

A typical HPLC separation profile of representative purified bulk sample is shown in FIG. 4. The purified urease product shows a prominent protein peak with a retention time between that of thyroglobulin (MW 669 kDa) and ferritin (MW 440 kDa). An apparent molecular weight of 550–600 kDa was estimated based on a series of runs. This peak was tentatively designated as hexameric urease. The area of this hexameric urease was at least 70% of the total protein in different lots of product.

A second prominent protein peak with a lower retention time (higher molecular weight) was also detected. The area of this peak ranged from 5–20%. This peak, with a molecular weight >600 kDa, was designated as octomeric urease. The total area of the octomeric plus hexameric urease peaks was over 90%.

These two characteristic peaks were isolated for further characterization. The two peaks were purified by HPLC from a preparation of reconstituted, freeze-dried urease and stored at 4° C. for over one week. During storage for this period of time, octomeric urease increases while the hexameric form decreases. The separated peak fractions were analyzed by reducing SDS-PAGE and ELISA reactivity with monoclonal and polyclonal antibodies to urease. On SDS-PAGE, both peaks showed urease A and B bands in comparable ratios. In addition, both showed nearly identical immunoreactivity in ELISA with polyclonal anti-urease holoenzyme antibodies (MPA3) and a monoclonal anti-UreB antibody (MAB71).

Enzymatic (urea hydrolytic) activity of recombinant urease

Three methods were used to investigate the enzymatic activity of recombinant urease: urease-specific silver staining following electrophoresis, the pH-sensitive phenol red urea broth assay, and direct detection of ammonia. Urease-specific silver staining, described by deLlano et al. (*Anal. Biochem.* 177:37–40, 1989), is based on the reaction of urease with urea to produce ammonia. The reaction leads to a localized increase in pH which facilitates a photographic redox reaction leading to disposition of metallic silver. Enzymatic activity of native *H. pylori* urease was detected with only a 1.0 µg sample. In contrast, 20 µg purified recombinant urease exhibited no urease activity.

The pH-sensitive phenol red broth assay, which is well known in the art, is based on a change in pH due to ammonia generation as a result of urea hydrolysis. Urease activity was demonstrated with as little as 0.2 µg/ml purified *H. pylori* urease. In contrast, no urease activity was associated with purified recombinant urease, even at concentrations up to 750 µg/ml.

Direct estimation of ammonia produced by hydrolysis of urea by urease was quantitated using Nesslers' reagent (Koch et al., *J. Am. Chem. Society* 46:2066–2069, 1924). Urease activity of native *H. pylori* urease was detectable at a concentration of 1 µg/ml. No activity was detected in assays containing up to 500 µg/ml purified recombinant urease.

Based on the results of the urease-specific silver staining assay, the pH-sensitive phenol red broth assay, and direct estimation of ammonia, there is no detectable urease activity in the recombinant urease product.

Protective and therapeutic activity of purified recombinant urease in animal infection models Since *H. pylori* does not readily infect laboratory animals, the *H. felis* model in rodents was used to test the efficacy of recombinant *H. pylori* urease in prophylaxis and antibacterial therapy. In this model, colonization of the stomach is readily established and is accompanied by gastric inflammation. This animal model is a well established system for the study of Helicobacter, and has been used extensively in laboratory investigations of the pathogenesis and treatment of Helicobacter-induced disease (Fox et al., *Infect. Immun.* 61:2309–2315, 1993; Goodwin & Worsley, *Helicobacter pylori*, Biology and Clinical Practice, CRC Press, Boca Raton, Fla., 465 pp, 1993). Antigenic cross-reactivity between *H. pylori* and *H. felis* ureases allows use of the human vaccine candidate of the invention, recombinant *H. pylori* urease (rUre), to immunize animals infected, or subsequently challenged, with *H. felis*.

Both germ-free and conventional mice are susceptible to orogastric challenge with *H. felis*, and develop life-long infection of the gastric epithelium, characterized by infiltration of inflammatory cells (Fox et al., ibid.). Dose response studies indicated that 100% of Swiss-Webster specific pathogen-free (SPF) mice become infected after a single oral challenge with $10^4$ *H. felis*. Unless otherwise specified, a single dose of $10^7$ was used to infect mice prior to therapeutic immunization or challenge mice after prophylactic immunization. A challenge of ~$10^3$ times the infectious dose (I.D.$_{90}$) with this Helicobacter spp. represents a severe test of immunity.

Assays for gastric infection

Several methods were used to detect Helicobacter in gastric tissue, including measurement of gastric urease activity, histologic examination, and culture of gastric tissue. Gastric urease activity was measured both qualitatively (presence or absence) and quantitatively. In the qualitative assay, stomachs were divided longitudinally into two halves, from the gastroesophageal sphincter to the pylorus. One longitudinal piece, representing approximately ¼ of the stomach, was placed in 1 mL of urea broth (0.1 g yeast extract, 0.091 g monopotassium phosphate, 0.095 g disodium phosphate, 20 g urea, and 0.1 g/L phenol red, pH 6.9). A distinctive color change (due to hydrolysis of urea by the enzyme, production of ammonia, and increased pH) after four hours incubation at room temperature indicated a positive result. For quantitative determinations, urease activity was determined by measuring absorbance at 550 nm of clarified urea broth incubated with whole stomach sections for 4 hours. This assay can detect as few as $1-2\times10^4$ *H. felis*/0.1 g stomach tissue. This assay provides the same sensitivity as commercially available urease test kits used for human samples. Commercial kits have proven to be 100% specific and 90–92% sensitive compared to biopsy/histology (Szeto et al., Postgrad. Med. J. 64:935–936, 1988: Borromeo et al. *J. Clin. Pathol.* 40:462–468, 1987).

Quantitative gastric urease assays by spectrophotometric measurement of $A_{550}$ were slightly more sensitive than visual determinations, and allowed estimation of the severity of infection. The cut-off value for a negative urease assay was defined as 2 standard deviations above the mean $A_{550}$ for unchallenged/uninfected mice. The cut-off for a positive gastric urease assay was defined by 2 standard deviations below the mean $A_{550}$ of unimmunized/challenged mice. Individual animals with low-grade infections had values intermediate between the negative and positive cut-offs. Visual grading of the urease response identified 11/12 (92%) of the positive samples.

Histologic examination was performed by fixing stomach tissue in 10% formalin. The tissue was then embedded in paraffin, sectioned and stained with a modified Warthin-Starry silver stain (Steiner's stain; Garvey, et al. Histotechnology 8:15–17, 1985) to visualize *H. felis*, and by hematoxylin and eosin (H & E) stain to assess inflammatory responses in the tissue. Stained sections were examined by an experienced pathologist blinded to the specimen code.

A semi-quantitative grading system was used to determine the number of bacteria and intensity of inflammation. The system used is a modification of the widely-accepted Sydney System for histological characterization of gastritis in humans (Price, Gastroenterol. Hepatol. 6:209–222, 1991). Full-thickness mucosal sections were examined for the intensity of inflammation (increase in lymphocytes, plasma cells, neutrophils and presence of lymphoid follicles) and depth of infiltration of these cells and graded on a scale of 0–4+. Grading the density of *H. felis* was accomplished by counting the number of bacterial cells with typical spiral morphology in an entire longitudinal section of gastric antrum (or corpus, if specified). Grades were assigned according to a range of bacteria observed (0=none; 1+=1–20 bacteria; 2+=21–50 bacteria; 3+=51–100 bacteria; and 4+=>100 bacteria).

Route of immunization

The effect of the route of administration upon the efficacy of the vaccine of the invention was examined in the mouse infection model. Six to eight week-old female specific pathogen free (SPF) Swiss-Webster mice were immunized with 200 μg recombinant *H. pylori* urease, either with or without 0.24M NaHCO$_3$. The recombinant urease was co-administered with 10 μg of cholera toxin (CT) as a mucosal adjuvant in all animals. Intragastric (IG) immunization was performed by delivering the antigen in 0.5 ml through a 20-gauge feeding needle to anesthetized animals. Oral immunization was performed by delivering the antigen in a 50 μl volume via a pipette tip to the buccal cavity of unanesthetized animals. For parenteral immunization, mice received 10 μg recombinant urease subcutaneously. Freund's complete adjuvant was used in the first subcutaneous immunization and Freund's incomplete adjuvant was used in subsequent boosters. For all routes of administration, a total of four doses of vaccine were administered at seven day intervals. Mice were challenged with $10^7$ *H. felis* two weeks after the final vaccine dose, and necropsied two weeks after challenge. Gastric *H. felis* infection was detected by urease activity and histology. Protection in an individual mouse was defined by a negative urease assay and by a 0 or 1+ bacterial score by histology.

Oral and intragastric administration of recombinant urease provided significant protection to challenge with *H. felis* (86–100%) (Table 1). Oral administration was effective both with and without co-administration of NaHCO$_3$ with the recombinant urease. Intragastric administration was more effective when the recombinant urease was co-administered with NaHCO$_3$. Parenteral injection of the vaccine antigen was least effective. Immunized mice had significantly lower numbers of bacteria in gastric tissue after challenge than unimmunized controls. IgA antibody responses in serum and secretions were highest in mice immunized by the oral route. IgA antibodies were not elicited by parenteral immunization.

TABLE 1

Recombinant *H. pylori* urease protects mice from challenge with *H. felis* after mucosal but not parental immunization

| VACCINE | ROUTE OF IMMUNIZATION | ADJUVANT | BICARBONATE[a] | % PROTECTED (# PROTECTED/TOTAL) UREASE ASSAY | HISTOLOGY[b] |
|---|---|---|---|---|---|
| PBS | oral | CT | No | 0 (0/8) | 0 (0/7) |
| 200 μg rUre | oral | CT | No | 100 (8/8)* | 100 (7/7)* |
| 200 μg rUre | oral | CT | Yes | 100 (7/7)* | 86 (6/7)* |
| 200 μg rUre | intragastric | CT | No | 75 (6/8)* | 38 (3/8) |
| 200 μg rUre | intragastric | CT | Yes | 100 (7/7)* | 100 (7/7)* |
| 10 μg rUre | subcutaneous | Freund's | NA | 38 (3/8) | 25 (2/8) |

[a]0.24 M sodium bicarbonate was administered with vaccine and adjuvant.
[b]Percent protected (number mice with 0–1+ bacterial score/number tested).
*p < 0.01, Fisher's exact test, compared to mice given CT alone.

The effect of immunization route upon the anti-urease antibody response was examined in mice. Swiss-Webster mice were immunized four times at ten day intervals with either: 1) 200 μg recombinant purified *H. pylori* urease with 10 μg CT, either with or without NaHCO$_3$, by oral administration; 2) 200 μg recombinant purified *H. pylori* urease and 10 μg CT with NaHCO$_3$, by intragastric administration; or 3) 10 μg recombinant purified *H. pylori* urease with Freund's adjuvant by subcutaneous administration. One week after the fourth vaccine dose, mucosal and serum antibody responses were examined by ELISA using microtiter plates coated with 0.5 μg of native *H. pylori* urease. Serum samples were diluted 1:100 and assayed for urease-specific IgA and IgG. Fresh fecal pellets, extracted with a protease inhibitor buffer (PBS containing 5% non-fat dry milk, 0.2 μg AEBSF, 1 μg aprotinin per ml, and 10 μM leupeptin), were examined for fecal anti-urease IgA antibody. In some experiments, fecal antibody values were normalized for total IgA content determined by ELISA, with urease-specific fecal IgA expressed in $A_{405}$ units/mg total IgA in each sample. Saliva samples were collected after stimulation with pilocarpine under ketamine anesthesia, and tested for urease-specific IgA at a dilution of 1:5.

No significant differences between antibody responses of mice immunized orally with or without NaHCO$_3$ were detected, and the data were pooled for analysis. Mice given subcutaneous antigen developed urease-specific serum IgG, but serum and fecal IgA responses were elicited only when antigen was delivered by mucosal routes (oral or intragastric).

Figure 5A:
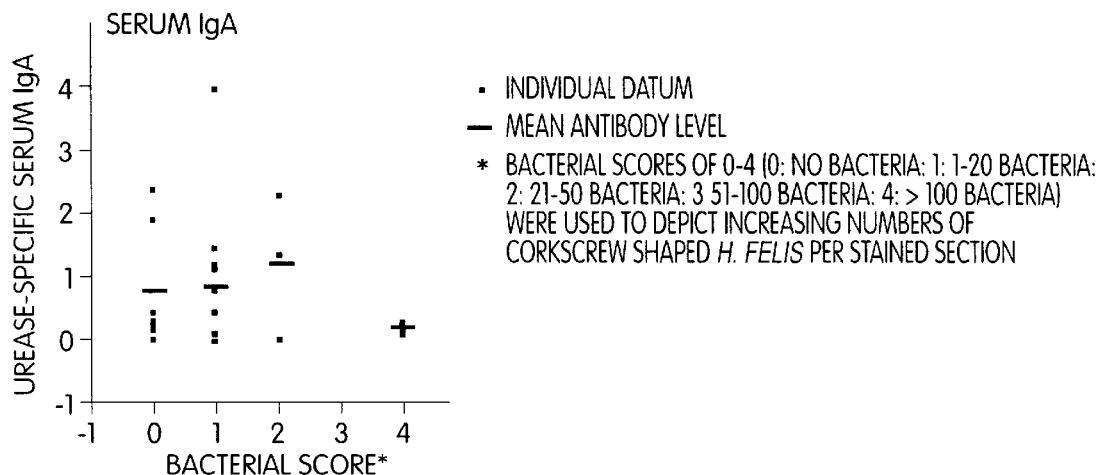
FIGS. 5A, 5B and 5C are graphs showing the bacterial score versus the levels of serum IgA, serum IgG, and fecal IgA antibodies from mice immunized with recombinant *H. pylori* urease and cholera toxin (CT).
Figure 5B:
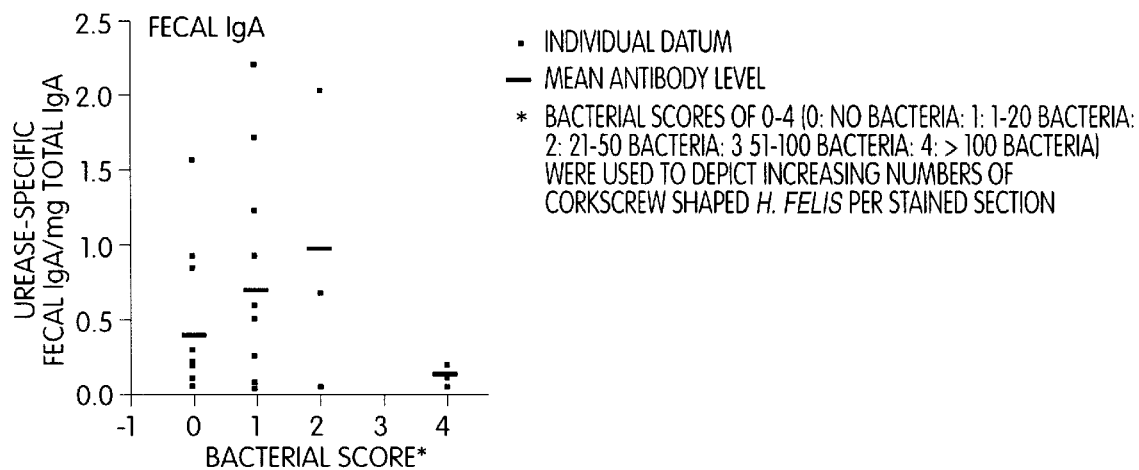
Figure 5C:
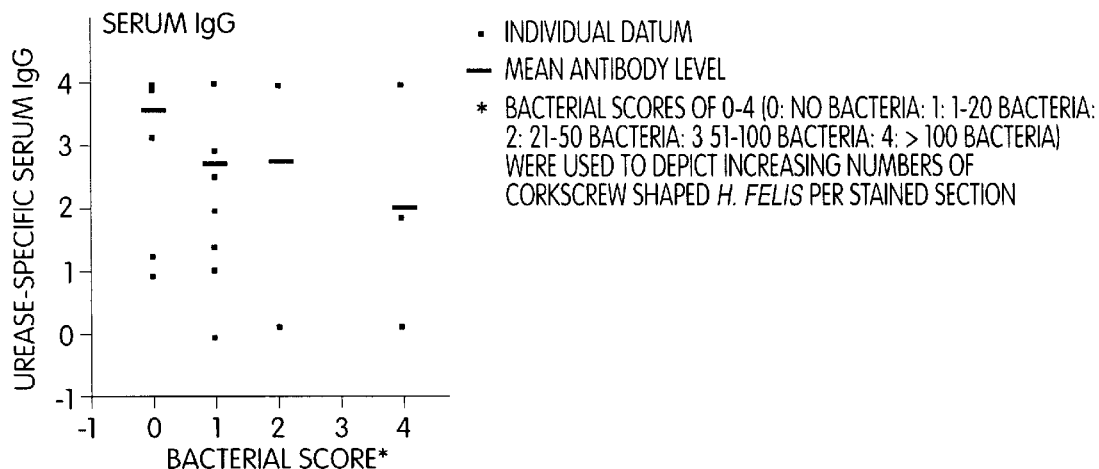
Figure 6A:
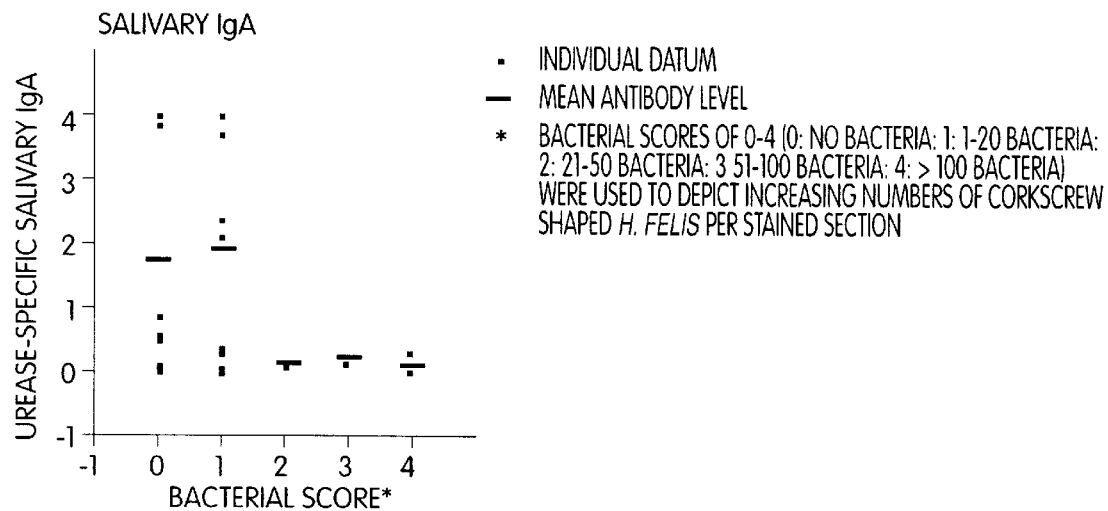
FIGS. 6A, 6B, 6C and 6D are graphs showing the bacterial score versus the levels of serum IgA, serum IgG, and fecal IgA antibodies from mice immunized with recombinant *H. pylori* urease and enterotoxigenic *E. coli* heat-labile toxin.
Figure 6B:
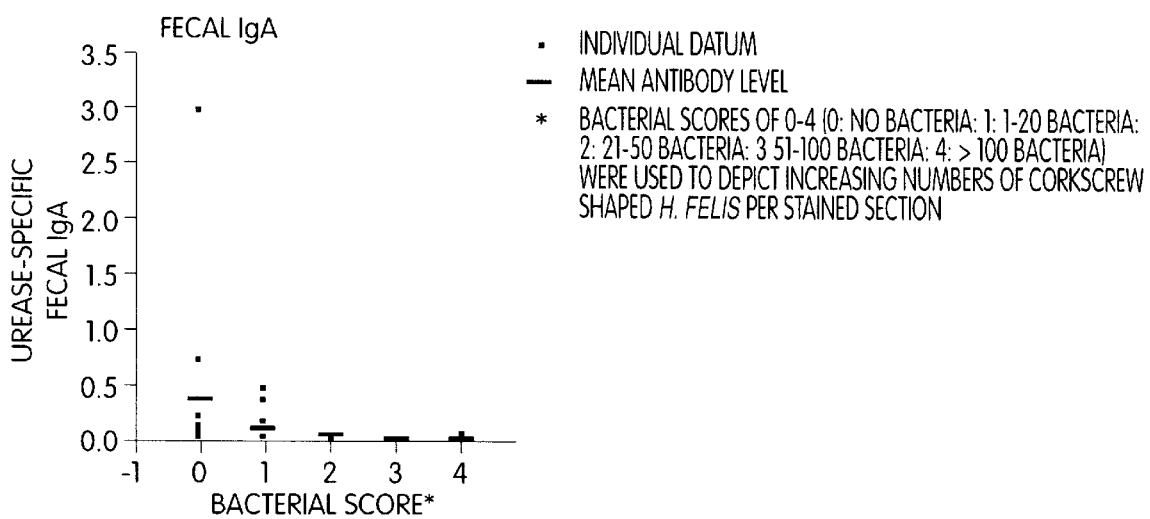
Figure 6C:
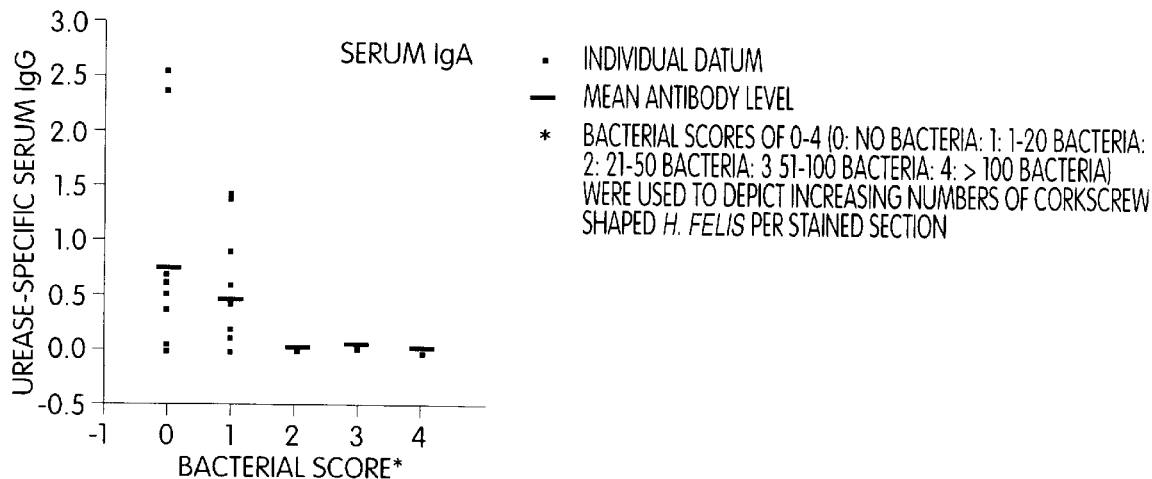
Figure 6D:
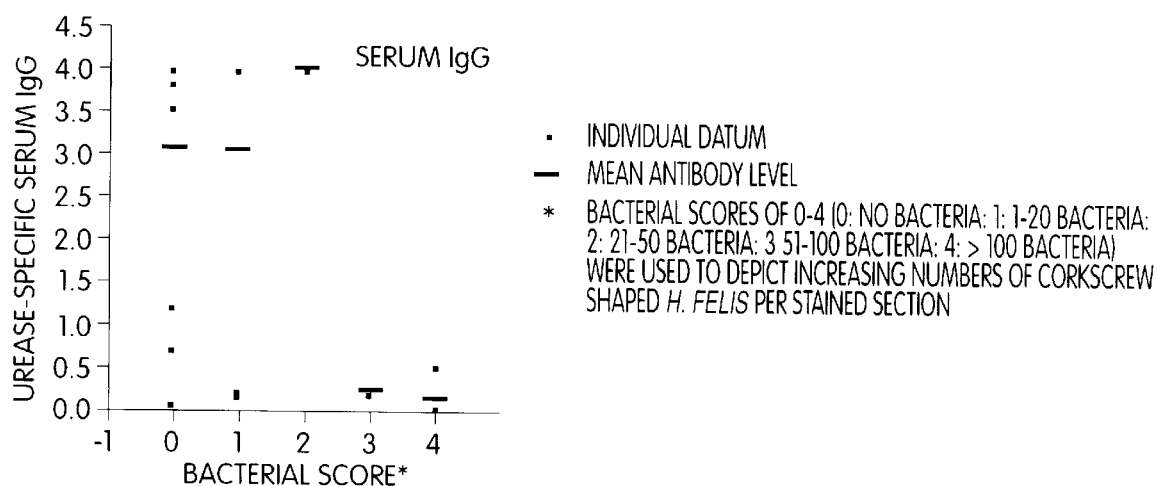
Figure 8A:
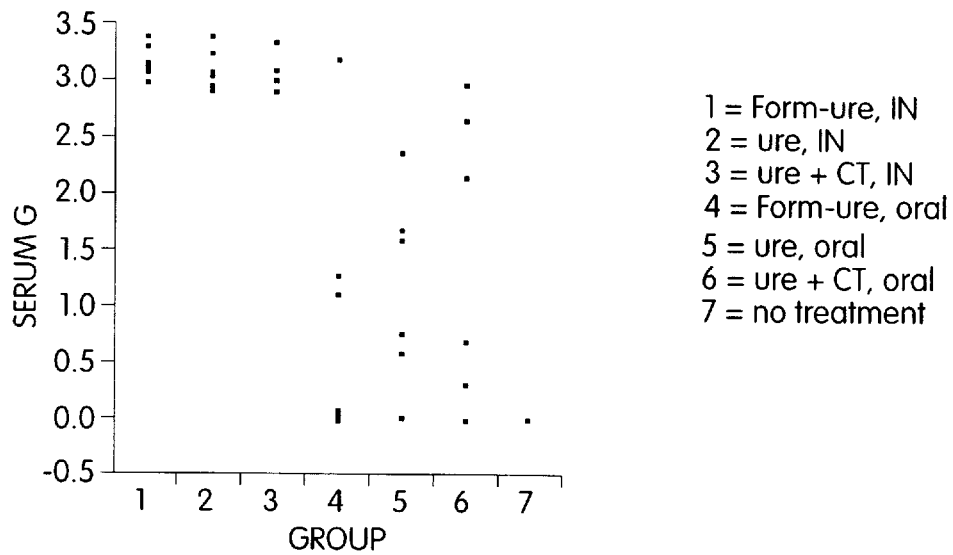
FIGS. 8A, 8B, 8C and 8D are graphs showing the serum IgG (Serum G), serum IgA (Serum A), fecal IgA (Fecal A), and salivary IgA (Sal A) levels in groups of mice treated according to the protocol illustrated in FIG. 7.
Figure 8B:
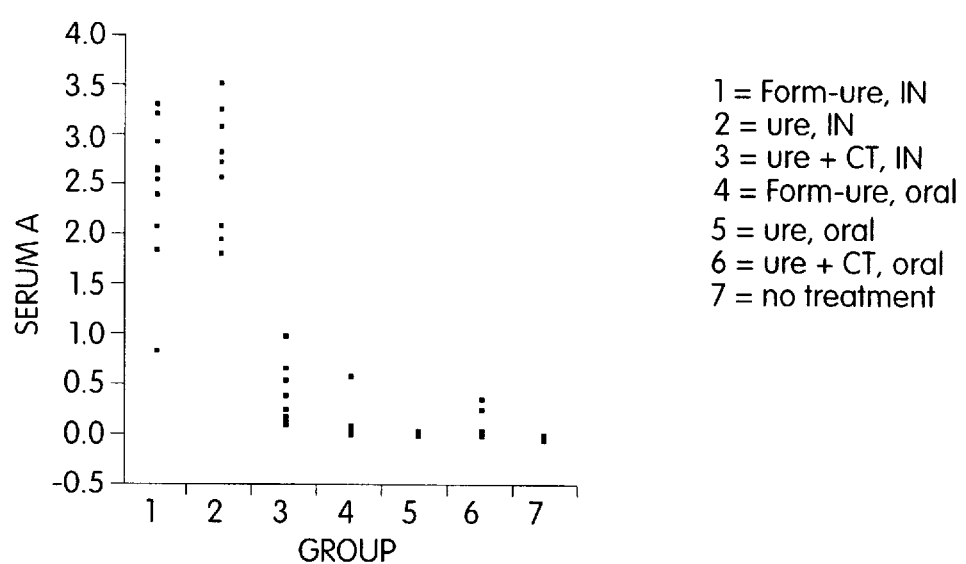
Figure 8C:
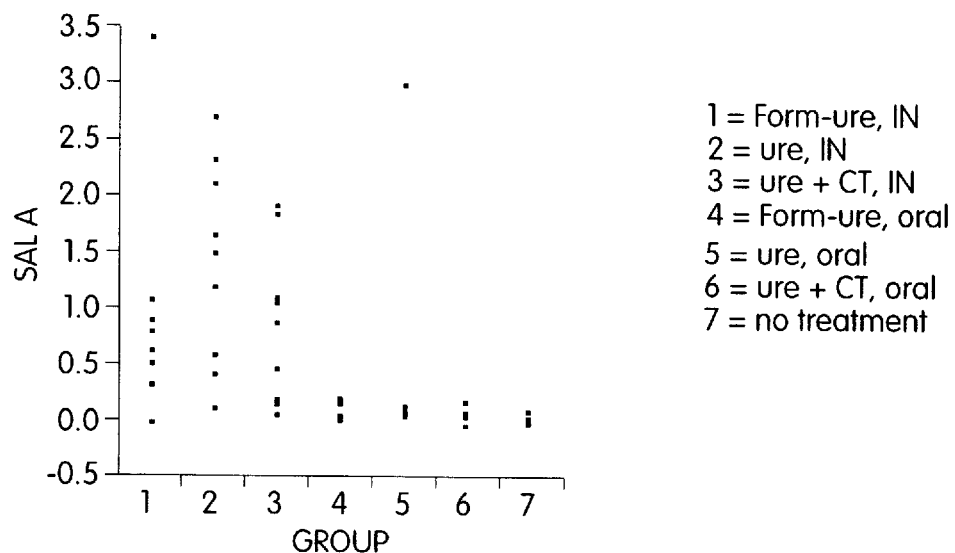
Figure 8D:
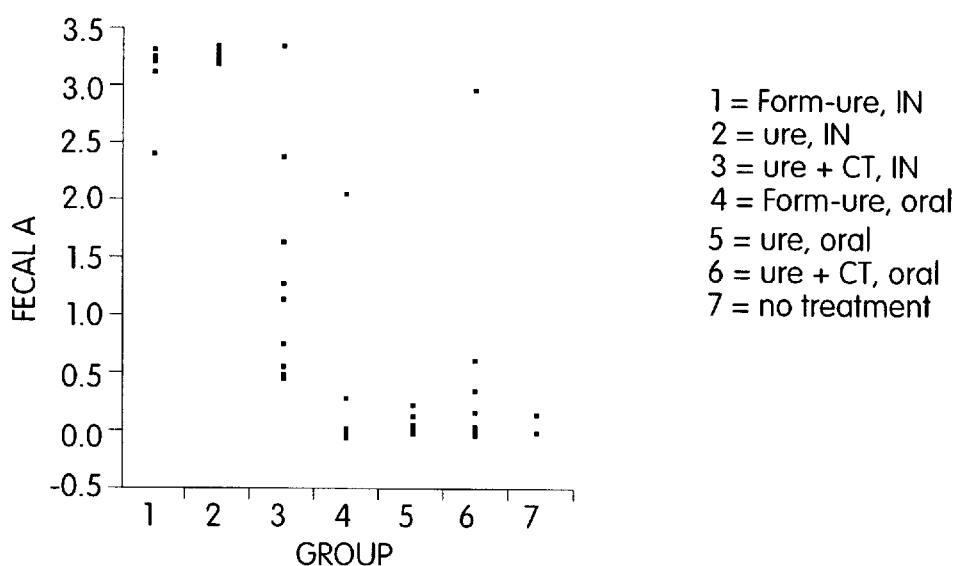

Mice immunized either orally or intragastrically with urease/CT were challenged with $10^7$ *H. felis*. The pre-challenge antibody levels of orally or intragastrically immunized mice were correlated with histologically-determined bacterial scores after *H. felis* challenge (FIGS. 5A, 5B and 5C). Although IgA responses varied considerably between individual mice, on the whole, mice with higher serum and fecal IgA levels had reduced bacterial scores. These data indicate a role for IgA in suppression of, and protection from, infection. In contrast, serum IgG antibodies did not correlate with protection. While some protected mice had no detectable IgA antibodies, high levels of anti-urease IgA were not observed animals that developed 4+ infections after challenge. These results not only support a role for mucosal immune responses in protection, but also suggest that immune mediators other than fecal and serum IgA play a role in eradication of *H. felis* infection.

These data show that: i) mucosal immunization is required for protective immunity; ii) the oral route of immunization is as effective, or more effective, than the intragastric route; iii) neutralization of gastric acid with NaHCO$_3$ is required for effective intragastric (but not oral) immunization; and iv) parenteral immunization does not stimulate mucosal immunity or provide effective protection against challenge.

Schedule of immunization

Alternative immunization schedules were compared in order to determine the optimal immunization time-table to elicit a protective mucosal immune response. Swiss-Webster mice were immunized with 100 μg recombinant urease in two, three, or four oral administrations, on a schedule shown in Table 2. The mucosal adjuvant CT (10 μg) was co-administered with the recombinant urease. As assessed by qualitative gastric urease assay, mice which received four weekly doses of antigen exhibited the highest levels of protection. Significant protection was also observed in mice given three doses of antigen on days 0, 7, and 21. Secretory IgA antibody responses were highest for mice given a total of four doses of recombinant urease at one week intervals. On the basis of protection ratio and antibody response, the latter schedule was selected for further evaluation of therapeutic and prophylactic vaccine activity.

TABLE 2

Effect of different schedules of oral immunization on the prophylactic efficacy of urease vaccine

| GROUP | VACCINE DOSE/ IMMUNIZATION (μg)[a] | SCHEDULE (DAY OF IMMUNIZATION) | % PROTECTED (#/TOTAL)[b] |
|---|---|---|---|
| 1 | 25 | 0, 7, 14, 21 | 70 (7/10)* |
| 2 | 50 | 0, 14 | 20 (2/10) |
| 3 | 50 | 0, 14 | 30 (3/9) |
| 4 | 33.3 | 0, 7, 21 | 40 (4/10)* |
| 5 | 50, 25, and 25 | 0, 7, 21 | 60 (6/10)* |
| 6 | None | 0, 7, 14, 21 | 0 (0/10) |

[a]Each group of mice were immunized orally with a total dose of 100 μg recombinant *H. pylori* urease. CT (10 μg) was used at each immunization, suspended in sterile distilled water, as the mucosal adjuvant. Group 6 received CT alone on the same schedule as group 1 and acted as the control. Groups 4 and 5 compared the effect of booster doses administered after two previous weekly immunizations.
[b]Percent protected (No. protected/No. tested) from a $10^7$ challenge dose of *H. felis* two weeks post-immunization. Mice were sacrificed two weeks after challenge and protection was determined by the qualitative gastric urease assay.
*p < 0.05, Fisher's exact test, compared to mice given CT alone.

The effect of different immunization schedules upon anti-urease antibody production was examined in mice.

Antibody responses of mice immunized by one of the five different immunization schedules described in Table 2 were examined. Significant protection was observed in mice that received vaccine in four weekly doses or two weekly doses with a boost on day 21. Mice immunized by either of these two immunization schedules also had the highest average immune responses. The serum IgG and salivary IgA levels were highest in mice vaccinated on a schedule of four weekly doses.

Dose-protection relationship

Graded doses of recombinant urease were orally administered to mice to determine the minimal and optimal doses required for immunization and protection. Recombinant urease doses of 5, 10, 25, 50, and 100 μg were administered to groups of eight mice by the oral route with 10 μg CT in PBS. The antigen was given on a schedule of four weekly doses. As assessed by gastric urease and histologic bacterial score, significant protection of mice against challenge with *H. felis* was observed at all doses, with no significant differences between dose groups (Table 3). A dose response effect was clearly demonstrated in serum and mucosal antibody responses to recombinant urease, with the highest immune response at the 100 μg dose level.

TABLE 3

Recombinant *H. pylori* urease at doses of 5 μg or more, protects mice against challenge with *H. felis*

| VACCINE | ADJUVANT | ROUTE OF IMMUNI-ZATION | % PROTECTED[A] (# PROTECTED/TOTAL) | |
|---|---|---|---|---|
| | | | UREASE ASSAY | HISTOLOGY |
| none | 10 μg CT | Oral | 0 (0/7) | 0 (0/7) |
| 5 μg rUre | 10 μg CT | Oral | 86 (6/7)* | 71 (5/7)* |
| 10 μg rUre | 10 μg CT | Oral | 88 (7/8)* | 63 (5/8)* |
| 25 μg rUre | 10 μg CT | Oral | 100 (9/9)* | 100 (9/9)* |
| 50 μg rUre | 10 μg CT | Oral | 100 (8/8)* | 88 (7/8)* |
| 100 μg rUre | 10 μg CT | Oral | 100 (7/7)* | 71 (5/7)* |

[a]Percent protected (number mice with 0–20 bacteria per section/number tested) as determined by examination of silver-stained stomach sections.
*Comparison to sham-immunized controls, Fisher's exact test, $p \leq 0.02$.

The effect of recombinant urease dosage upon the antiurease antibody response was examined in mice. Swiss-Webster mice were immunized orally with graded doses (0, 5, 10, 25, 50, or 100 μg) of recombinant urease plus 10 μg CT as a mucosal adjuvant. IgA antibody responses in serum, feces, and saliva increased with the amount of recombinant urease administered. A 100 μg dose of recombinant urease produced the highest antibody levels.

Swiss-Webster mice were orally immunized with graded doses (0, 5, 25, or 100 μg) of recombinant urease, with 25 μg enterotoxigenic *E. coli* heat-labile toxin (LT) as a mucosal adjuvant. One group of mice received 25 μg recombinant urease and 10 μg CT as a mucosal adjuvant for comparison. The mice were immunized orally 4 times every 7 days. Serum, feces, and saliva were collected 10 to 13 days after the last immunization and urease-specific antibody levels were determined by ELISA. Mice immunized with recombinant urease and LT developed serum and secretory antibodies against urease, with a clear dose-response effect. Strong salivary IgA antibody responses were observed in these animals.

Mice immunized with urease and LT as described above were challenged with $10^7$ *H. felis* (see FIG. 4). The pre-challenge antibody responses of the urease/LT immunized mice were correlated with histologically-determined bacterial scores (FIGS. 6A, 6B 6C and 6D). Fully protected animals (0 bacterial score) and those with low-grade infections (1+ bacterial score) had higher levels of antibodies in all compartments than animals with more severe infections. A few protected mice had no detectable immune response, suggesting that immune mediators other than IgA antibodies play a role in eradication of *H. felis* infection.

The ability of high doses of recombinant urease to elicit a mucosal immune response was examined by administering intragastrically 1 μg, 200 μg, or 5 mg without adjuvant. One group of mice were intragastrically immunized with 200 μg urease plus 10 μg CT as a control. Blood, feces, and saliva were collected 5 to 8 days after the last immunization. Animals were then challenged with $10^7$ *H. felis* 10 days after the last immunization and sacrificed 14 days after challenge. *H. felis* infection was detected by urease activity in stomach tissue.

High doses of recombinant urease elicited urease-specific serum IgG, but elicited comparatively low levels of mucosal antibodies as detected by ELISA. Animals which exhibited a urease-specific serum IgG response were fully susceptible to *H. felis* challenge, indicating that serum IgG does not play a role in protection.

In summary, data from the above experiments to investigate different administration routes, administration schedules, and mucosal adjuvants demonstrate that, when administered with an effective mucosal adjuvant, oral or intragastric administration of recombinant urease at relatively low doses elicits secretory IgA antibody and serum IgA and IgG responses. Secretory IgA antibody provides protection while serum IgG responses do not. When protection is measured by histological bacterial counts, animals with higher IgA antibody titers were fully protected, or had significantly reduced infections, compared to animals with lower IgA antibody titers. Animals which did not exhibit detectable IgA antibody levels developed severe infections after challenge. Antibody responses were dose-dependent and differed by the schedule of administration of antigen. The highest levels were achieved at antigen doses of 100–200 μg. Administration of four doses of antigen at one week intervals provided the optimal schedule for immunization.

An additional administration route, intranasal, was investigated, as follows:

Intranasal vaccination with recombinant urease

Swiss Webster mice were immunized either orally or intranasally (IN) with recombinant urease, or formalin-fixed urease. The amounts of antigen and adjuvant, routes of administration (IN or oral), and immunization schedules are shown in FIG. 7. The formalin-fixed urease (Form-ure) was prepared according to the following protocol:

(1) 1 mg vial of recombinant urease is reconstituted with 150 μL of RO/DI water;

(2) 50 μL of formalin (37% formaldehyde) diluted 1:1000 in RO/DI water is added to the 1 mg vial (final concentration of urease is 5 mg/ml);

(3) the vial is then incubated at 35° C. for 48 hours.

Serum IgG, IgA, fecal IgA and salivary IgA responses in IN+CT group were higher than the oral+CT group, despite higher doses of rUrease and adjuvants that were used for oral immunization (FIG. 7 and Table 4).

Protection was measured by urease test, as well as by determining bacterial score on stomach tissues of sacrificed animals. One hundred percent protection was found in the IN group, as compared to 80% in the oral group when protection was assayed by urease test. Seven of eight mice from orally immunized animals were positive for bacteria on their stomach tissues, whereas only 1/10 of IN group was positive for bacteria (see groups 3 and 6 in Table 4 and FIGS. 8A, 8B, 8C, and 8D).

In a second experiment, mice were immunized either intragastrically (IG) or intranasally with rUrease co-administered with LT as mucosal adjuvant (see FIG. 9 for details of experiment and immunization schedule). In this experiment, serum IgG, IgA and saliva IgA responses in the IN+LT group were higher than the IG+LT group, despite higher doses of antigen and adjuvant that were used for IG immunizations (FIGS. 10A 10B, 10C 10D and 10E, and Table 5, groups 4 and 8). Mice in the IN+LT group were fully protected against *H. felis* challenge (10/10 compared with 3/9 untreated group) as assessed by urease test (see groups 4 and 5 of Table 5).

TABLE 4

| Mouse # | Urease treatment | Route/adj. | serum G | serum A | fecal A | salivary A | 4 h urease | Bact. | Path. |
|---|---|---|---|---|---|---|---|---|---|
| 1A1 | 10 μg/HCHO | IN/none | 3.398 | 3.318 | 3.377 | 3.339 | + | | |
| 1A2 | | | 3.119 | 3.218 | 0.786 | 3.249 | + | | |
| 1A3 | | | 2.967 | 2.535 | 0.593 | 3.153 | | | |
| 1A4 | | | 3.064 | 2.390 | 1.065 | 3.311 | + | | |
| 1A5 | | | 3.009 | 2.647 | 0.617 | 3.244 | + | | |
| 1B1 | | | 2.994 | 2.068 | 0.497 | 3.329 | − | | |
| 1B2 | | | 3.099 | 2.611 | −0.010 | 3.235 | + | | |
| 1B3 | | | 3.306 | 1.823 | 0.323 | 3.295 | + | | |
| 1B4 | | | 3.424 | 2.931 | 0.522 | 3.372 | + | | |
| 1B5 | | | 3.175 | 0.832 | 0.803 | 2.439 | + | | |
| 2A1 | 10 μg | IN/none | 3.021 | 2.562 | 2.090 | 3.204 | + | | |
| 2A2 | | | 2.971 | 2.806 | 1.475 | 3.304 | + | | |
| 2A3 | | | 2.894 | 1.943 | 0.584 | 3.288 | + | | |
| 2A4 | | | 2.918 | 2.804 | 2.291 | 3.363 | + | | |
| 2A5 | | | 2.926 | 3.264 | 0.118 | 3.418 | + | | |
| 2B1 | | | 3.220 | 3.505 | 1.634 | 3.415 | + | | |
| 2B2 | | | 3.383 | 2.708 | 0.410 | 3.336 | + | | |
| 2B3 | | | 3.092 | 1.814 | 0.411 | 3.253 | + | | |
| 2B4 | | | 3.033 | 3.090 | 2.672 | 3.266 | + | | |
| 2B5 | | | 3.055 | 2.076 | 1.193 | 3.263 | + | | |
| 3A1 | 10 μg | IN/CT | 2.969 | 0.405 | 0.192 | 1.670 | − | 0 | 2 |
| 3A2 | | | 2.871 | 0.097 | 0.154 | 0.526 | − | 0 | 2 |
| 3A3 | | | 2.984 | 0.677 | 0.081 | 0.473 | | | |
| 3A4 | | | 3.092 | 0.563 | 1.824 | 3.398 | − | | |
| 3A5 | | | 3.335 | 0.256 | 1.052 | 0.587 | − | 1 | 2 |
| 3B1 | | | 3.013 | 0.148 | 0.142 | 0.586 | − | 0 | 2 |
| 3B2 | | | 3.068 | 0.388 | 0.867 | 2.410 | − | 0 | 2 |
| 3B3 | | | 3.008 | 0.255 | 0.468 | 0.778 | − | 0 | 2 |
| 3B4 | | | 2.908 | 0.985 | 1.086 | 1.172 | − | 0 | 2 |
| 3B5 | | | 2.879 | 0.186 | 1.904 | 1.317 | − | 0 | 2 |
| 4A1 | 100 μg/HCHO | oral/none | −0.006 | 0.024 | 0.021 | 0.009 | + | | |
| 4A2 | | | 0.050 | 0.097 | 0.079 | 0.041 | + | | |
| 4A3 | | | 0.001 | 0.097 | 0.056 | −0.019 | + | | |
| 4A4 | | | 3.195 | 0.598 | 0.190 | 2.097 | + | 0 | 3 |
| 4A5 | | | 1.271 | 0.027 | 0.034 | 0.010 | + | | |
| 4B1 | | | 0.096 | 0.045 | 0.165 | 0.309 | + | | |
| 4B2 | | | 0.021 | 0.033 | 0.043 | 0.059 | + | | |
| 4B3 | | | 1.109 | 0.055 | 0.080 | 0.019 | + | | |
| 4B4 | | | 0.006 | 0.022 | 0.083 | 0.017 | + | | |
| 4B5 | | | 0.013 | 0.027 | 0.039 | 0.010 | + | | |
| 5A1 | 100 μg/— | oral/none | 0.032 | 0.042 | 0.151 | 0.030 | + | | |
| 5A2 | | | 0.756 | 0.077 | 2.957 | 0.156 | + | | |
| 5A3 | | | 2.362 | 0.075 | .0.104 | 0.262 | + | | |
| 5A4 | | | 0.012 | 0.034 | 0.146 | 0.065 | + | | |
| 5A5 | | | 0.011 | 0.035 | 0.163 | 0.013 | + | | |
| 5B1 | | | 0.012 | 0.042 | 0.089 | 0.017 | + | | |
| 5B2 | | | 0.017 | 0.017 | 0.076 | 0.049 | + | | |
| 5B3 | | | 1.583 | 0.058 | 0.058 | 0.182 | +/− | | |
| 5B4 | | | 0.602 | 0.030 | 0.093 | 0.093 | + | | |
| 5B5 | | | 1.672 | 0.059 | 0.060 | 0.093 | + | | |
| 6A1 | 25 μg/— | oral/CT | 0.698 | 0.267 | 0.076 | 0.387 | − | 1 | 2 |
| 6A2 | | | 2.139 | 0.065 | 0.089 | 0.206 | − | 1 | 2 |
| 6A3 | | | 0.006 | 0.013 | 0.098 | 0.011 | − | 3 | 2 |
| 6A4 | | | 2.957 | 0.354 | 0.185 | 2.999 | − | 1 | 2 |
| 6A5 | | | 0.011 | 0.019 | 0.042 | 0.026 | − | 0 | 2 |
| 6B1 | | | 0.000 | 0.022 | 0.041 | 0.005 | − | 1 | 2 |
| 6B2 | | | 0.009 | 0.002 | 0.067 | 0.069 | − | 2 | 2 |
| 6B3 | | | 0.320 | 0.022 | 0.041 | 0.048 | + | 4 | 2 |
| 6B4 | | | 0.010 | 0.009 | −0.021 | 0.023 | + | 4 | 2 |
| 6B5 | | | 2.633 | 0.090 | 0.047 | 0.647 | − | 1 | 2 |
| 7A1 | none | | 0.011 | 0.018 | 0.074 | 0.019 | + | 4 | 1 |
| 7A2 | | | 0.007 | 0.025 | 0.042 | −0.004 | + | 4 | 2 |
| 7A3 | | | 0.000 | 0.019 | 0.082 | 0.018 | + | 4 | 2 |
| 7A4 | | | 0.004 | 0.028 | 0.024 | −0.002 | + | 4 | 2 |
| 7A5 | | | 0.011 | 0.005 | 0.041 | 0.029 | X | | |
| 7B1 | | | 0.019 | 0.004 | 0.089 | −0.005 | + | 4 | 1 |

TABLE 4-continued

| Mouse # | Urease treatment | Route/adj. | serum G | serum A | fecal A | salivary A | 4 h urease | Bact. | Path. |
|---|---|---|---|---|---|---|---|---|---|
| 7B2 | | | 0.006 | −0.003 | −0.009 | 0.008 | + | 4 | 2 |
| 7B3 | | | 0.006 | 0.024 | 0.066 | 0.167 | + | 4 | 2 |
| 7B4 | | | 0.015 | 0.018 | 0.063 | 0.018 | + | 4 | 1 |
| 7B5 | | | 0.007 | 0.023 | 0.111 | 0.011 | + | | |
| plate 1 controls | | | | | | | | | |
| + | | | 2.265 | 3.280 | 1.651 | 3.315 | | | |
| − | | | −0.010 | 0.040 | 0.065 | 0.056 | | | |
| plate 2 controls | | | | | | | | | |
| + | | | 1.969 | 3.289 | 1.700 | 3.298 | | | |
| − | | | −0.001 | 0.034 | −0.004 | 0.019 | | | |

TABLE 5

| Mouse # | Treatment | serum G | serum A | salivary A | 2 week sac A (550) |
|---|---|---|---|---|---|
| 1AN | 25 μg 5X IN | 3.530 | 0.350 | 0.340 | 0.802 |
| 1AL | 200 μg 2X IG | 3.263 | 0.154 | 1.544 | 0.768 |
| 1AR | | 3.231 | 0.630 | 0.204 | 0.805 |
| 1ALL | | 3.233 | 0.318 | 0.251 | 0.806 |
| 1BN | | 3.344 | 0.401 | 0.112 | 0.726 |
| 1BL | | 3.322 | 0.724 | 2.015 | 0.168 |
| 1BR | | 3.424 | 0.225 | 0.426 | 0.748 |
| 1BLL | | 3.285 | 0.591 | 0.719 | 0.807 |
| 1BRR | | 3.262 | 0.141 | 0.202 | 0.675 |
| 2AN | 25 μg 5X IN | 3.164 | 0.054 | 0.014 | 0.814 |
| 2AL | 200 μg 1X IG | 3.232 | 0.231 | 0.747 | 0.823 |
| 2AR | | 3.236 | 0.981 | 0.412 | 0.695 |
| 2ALL | | 3.303 | 0.122 | 0.832 | 0.813 |
| 2BN | | 3.357 | 0.690 | 0.993 | 0.747 |
| 2BL | | 3.264 | 1.002 | 0.840 | 0.704 |
| 2BR | | 3.284 | 1.377 | 0.934 | 0.161 |
| 2BLL | | 3.241 | 0.458 | 0.191 | 0.748 |
| 2BRR | | 3.280 | 0.129 | 0.134 | 0.720 |
| 3AN | 25 μg 2X IN | 0.165 | 0.031 | 0.001 | 0.791 |
| 3AL | 200 μg 2X IG | 3.364 | 0.332 | 0.356 | 0.824 |
| 3AR | | 1.731 | 0.031 | −0.003 | 0.810 |
| 3ALL | | 3.321 | 0.450 | 0.541 | 0.798 |
| 3ARR | | 3.358 | 0.158 | 0.001 | 0.675 |
| 3BN | | 3.199 | 0.276 | 0.212 | 0.820 |
| 3BL | | 3.174 | 2.463 | 2.838 | 0.839 |
| 3BR | | 3.274 | 0.607 | 1.517 | 0.481 |
| 3BLL | | 3.284 | 1.279 | 2.593 | 0.829 |
| 3BRR | | 3.254 | 0.427 | 1.684 | 0.852 |
| 4AN | 25 μg 4X IN | 3.375 | 0.118 | 0.212 | 0.111 |
| 4AL | with 2 μg LT | 3.482 | 0.346 | 0.546 | 0.107 |
| 4AR | | 3.330 | 3.237 | 3.302 | 0.109 |
| 4ALL | | 3.343 | 3.067 | 3.229 | 0.103 |
| 4ARR | | 3.220 | 1.625 | 2.156 | 0.106 |
| 4BN | | 3.287 | 1.263 | 2.943 | 0.224 |
| 4BL | | 3.305 | 0.496 | 2.029 | 0.139 |
| 4BR | | 3.283 | 0.809 | 2.307 | 0.114 |
| 4BLL | | 3.313 | 1.019 | 3.346 | 0.106 |
| 4BRR | | 3.474 | 0.674 | 1.683 | 0.119 |
| 5AN | none | 0.075 | 0.023 | 0.001 | 0.26 |
| 5AL | | 0.005 | 0.016 | −0.002 | 0.881 |
| 5AR | | 0.011 | 0.008 | −0.001 | 0.839 |
| 5ARR | | 0.005 | 0.007 | 0.000 | 0.834 |
| 5BN | | 0.033 | 0.016 | 0.001 | 0.134 |
| 5BL | | 0.013 | 0.009 | 0.004 | 0.814 |
| 5BR | | 0.025 | 0.014 | 0.007 | 0.833 |
| 5BLL | | 0.028 | 0.019 | 0.008 | 0.155 |
| 5BRR | | 0.095 | 0.012 | 0.003 | 0.818 |
| 6AN | 25 μg 5X IN | 3.353 | 0.680 | 0.498 | |
| 6AL | 200 μg 2X IG | 3.470 | 0.248 | 0.100 | |
| 6AR | | 3.387 | 1.236 | 0.741 | |
| 6ALL | | 3.362 | 0.409 | 0.322 | |
| 6ARR | | 3.244 | 1.036 | 1.056 | |
| 6BN | | 3.211 | 2.749 | 2.014 | |
| 6BL | | 3.286 | 0.360 | 0.328 | |
| 6BR | | 8.269 | 0.749 | 1.882 | |
| 6BLL | | 3.347 | 0.275 | 0.030 | |
| 6BRR | | 3.321 | 0.311 | 0.989 | |
| 7AN | 25 μg 4X IN | 3.415 | 0.756 | 2.584 | |
| 7AL | with 2 μg LT | 3.428 | 3.080 | 3.287 | |
| 7AR | | 3.249 | 2054 | 3.188 | |
| 7ALL | | 3.269 | 1.010 | 3.240 | |
| 7ARR | | 3.255 | 0.713 | 3.243 | |
| 7BN | | 3.310 | 3.081 | 3.274 | |
| 7BL | | 3.439 | 2.298 | 3.222 | |
| 7BR | | 3.359 | 1.026 | 1.757 | |
| 7BLL | | 3.370 | 1.441 | 3.025 | |
| 7BRR | | 3.330 | 0.689 | 1.169 | |
| 8AN | 200 μg 4X IG | 0.281 | 0.031 | 0.000 | |
| 8AL | with 10 μg LT | 3.234 | 0.925 | 1.872 | |
| 8AR | | 3.285 | 0.827 | 2.751 | |
| 8ALL | | 3.313 | 0.547 | 0.395 | |
| 8ARR | | 3.363 | 0.382 | 1.144 | |
| 8BN | | 3.407 | 1.189 | 1.880 | |
| 8BR | | 3.315 | 1.608 | 2.536 | |
| 8BLL | | 3.271 | 0.438 | 0.599 | |
| 9AN | none | 0.011 | 0.003 | 0.000 | |
| 9AL | | 0.017 | 0.005 | 0.001 | |
| 9AR | | 0.007 | 0.002 | 0.001 | |
| 9ALL | | 0.011 | 0.013 | 0.000 | |
| 9ARR | | 0.006 | 0.019 | −0.002 | |
| 9BN | | 0.017 | 0.010 | −0.001 | |
| 9BL | | 0.020 | 0.008 | −0.002 | |
| 9BR | | 0.031 | 0.012 | −0.002 | |
| 9BLL | | 0.005 | 0.016 | 0.005 | |
| 95BRR | | 0.019 | 0.011 | 0.000 | |

Figure 11:
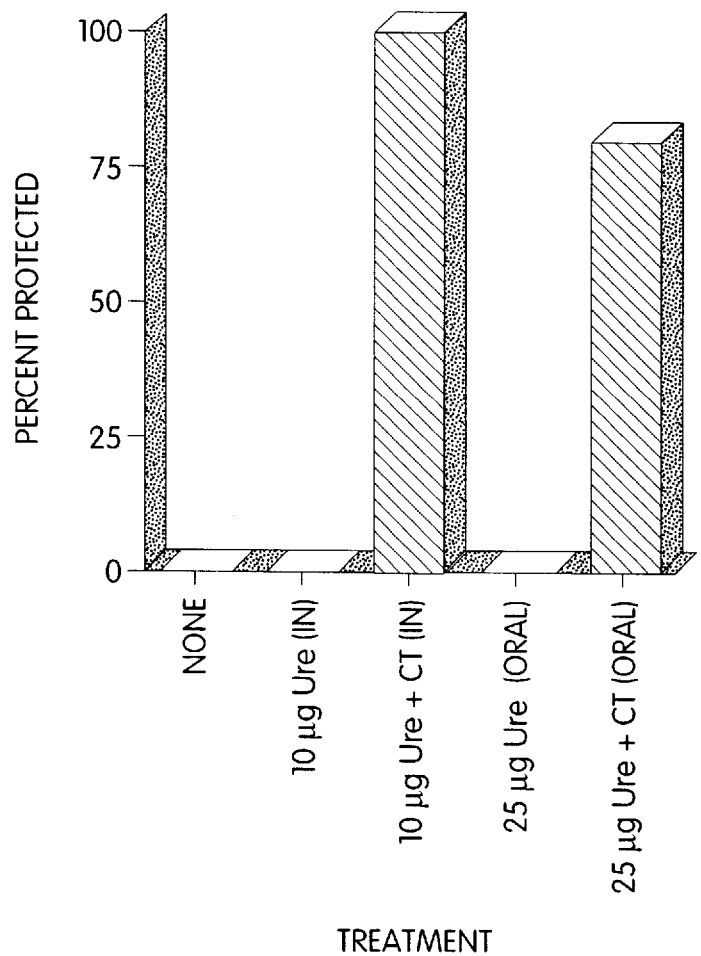
FIG. 11 is a graph showing that rUrease (10 $\mu$g) given by the intranasal route with CT (5 $\mu$g) is at least as effective as rUrease (25 μg) given by the oral route with CT (10 μg) in preventing infection with H. felis.

Further support for the efficacy of intranasal immunization is shown in FIG. 11. Briefly, this experiment showed that rUrease (10 μg) administered by the intranasal route with CT (5 μg) is at least as effective as rUrease (25 μg) given by the oral route with CT (10 μg) in preventing infection with H. felis.

Selection of a mucosal adjuvant

E. coli heat-labile toxin (LT), a multisubunit toxin with A and B components, is closely related, both biochemically and immunologically, to CT. Because the toxicity of LT is lower than CT, LT is likely to be more acceptable as a mucosal adjuvant for use in humans (Walker and Clements, Vaccine Res. 2:1–10, 1993).

Mice were orally immunized with 5 μg, 25 μg, or 100 μg recombinant urease and 25 μg recombinant LT (Swiss Serum Vaccine Institute, Berne, Switzerland) for a total of four weekly doses. Controls received LT only, or 25 μg urease vaccine with CT. Mice were challenged two weeks after the fourth dose and necropsied two weeks after challenge.

Gastric urease assays indicated significant protection or suppression of the infection in immunized animals at all vaccine doses (Table 6). Histological assessment confirmed significant reductions in bacterial scores in mice which received ≤5 μg urease and LT. Protection was directly correlated with dose as determined by both gastric urease assay and histological examination, with the highest protection conferred by 100 μg of recombinant urease co-administered with LT. Antibody determinations confirmed a dose-response relationship, with highest mucosal immune responses at the 100 μg dose. When recombinant urease was administered at equivalent doses (25 μg), LT was superior to CT as a mucosal adjuvant. These data indicate that while CT enhances the mucosal immune response to orally administered recombinant urease, LT is a better mucosal adjuvant and is thus the preferred over CT for co-administration with recombinant urease.

TABLE 6

E. coli heat-labile enterotoxin (LT) as a mucosal adjuvant for immunization with recombinant H. pylori urease

| VACCINE | ADJUVANT | % PROTECTED (# PROTECTED/TOTAL)[a] | |
|---|---|---|---|
| | | UREASE ASSAY | HISTOLOGY |
| None | 25 μg LT | 0 (0/9) | 0 (0/9) |
| 25 μg rUre | 10 μg CT | 70 (7/10)* | 60 (6/10)* |
| 5 μg rUre | 25 μg LT | 787 (7/9)* | 56 (5/9)* |
| 25 μg rUre | 25 μg LT | 90 (9/10)* | 80 (8/10)* |
| 100 μg rUre | 25 μg LT | 100 (8/8)* | 100 (8/8)* |

[a]Percent protected (number of mice with negative urease assay or bacterial score 0–1+/number tested) determined by bacterial scores of silver-stained stomach sections.
*Comparison to sham-immunized controls, Fisher's exact test, p < 0.03.

To determine the adjuvant activity of lower doses of LT, mice were orally immunized with 25 μg of recombinant urease administered with 1, 5, 10, or 25 μg of LT. Similar protection ratios and antibody responses were observed at all LT doses.

Several studies were performed to assess adjuvants other than CT and LT, and to determine whether the requirement for a mucosal adjuvant could be eliminated by administration of antigen alone at a high dose. Cholera toxin B subunit (CTB) was compared with CT as a mucosal adjuvant for urease immunization. No protective effect was observed when 200 μg urease was co-administered intragastrically with 100 μg CTB (Calbiochem, La Jolla, Calif.) in 0.24M sodium bicarbonate, whereas the same amount of urease with 10 μg CT gave 100% protection as assessed by gastric urease activity.

An orally-active semi-synthetic analogue of muramyl dipeptide, GMDP, (N-acetylgluosaminyl-(b1-4)-N-acetyl-muramyl-L-alanyl-D-isoglutamine), was co-administered with 25 μg urease at doses of 2, 20, and 200 μg. GMDP co-administered with recombinant urease failed to protect mice against H. felis challenge.

Large doses (200 μg, 1 mg, or 5 mg) of recombinant urease with or without CT were intragastrically administered to mice once a week for four weeks. The intragastric route was required because volumes for high antigen doses exceeded those that could be given orally in a reproducible fashion. NaHCO$_3$ was co-administered to neutralize gastric acid. A total of four doses of antigen were administered at ten day intervals. Blood, feces, and saliva were collected five to eight days after the last immunization. Animals were challenged with 1×10$^7$ H. felis, and infection was determined by urease activity in stomach tissue.

In the absence of CT, high antigen doses did not confer protection against H. felis challenge, whereas controls given 200 μg of recombinant urease with CT were significantly protected (Table 7). Urease-specific serum IgG was induced at the high recombinant urease doses without adjuvant, but serum, fecal, and salivary IgA responses were absent or minimal. Histological examination of coded specimens from animals given 5 mg doses of urease revealed no differences in bacterial scores or leukocytic infiltrates, compared with sham-immunized animals.

TABLE 7

A mucosal adjuvant facilitates protection by recombinant urease

| Vaccine | Adjuvant | % protected (# protected/ tested) | Mean antibody levels (±SD) before challenge[a] | | | |
|---|---|---|---|---|---|---|
| | | | Serum IgG | Serum IgG | Fecal IgA | Salivary IgA |
| none | PBS | 0 (0/5) | 0.01 (±0.00) | 0.03 (±0.07) | 0.01 (±0.02) | 0.02 (±0.03) |
| 200 μg rUre | 10 μg CT | 88 (7/8)* | >2.97 (±1.84) | >1.02 (±1.41) | 0.16 (±0.14) | 0.59 (±0.73) |
| 200 μg rUre | none | 0 (0/9) | >2.06 (±1.98) | 0.07 (±0.11) | 0.02 (±0.02) | 0.06 (±0.13) |
| 1 mg rUre | none | 0 (0/9) | >3.28 (±1.48) | 0.12 (±0.17) | 0.02 (±0.03) | 0.18 (±0.40) |
| 5 mg rUre | none | 0 (0/9) | >2.68 (±1.98) | >0.22 (±0.17) | 0.02 (±0.02) | 0.08 (±0.11) |

[a]Mean (±SD) urease-specific serum IgG or IgA expressed as A$_{405}$ units of serum (diluted 1:100), fecal extract (diluted 1:20), or saliva (diluted 1:5). Means are shown as > when individual values of 4.0 (the maximum A$_{405}$ reading) were included in calculating the mean values.
*Comparison to sham-immunized controls, Fisher's exact test, p = 0.005.

Therapeutic immunization of mice with H. felis gastritis

Figure 12:
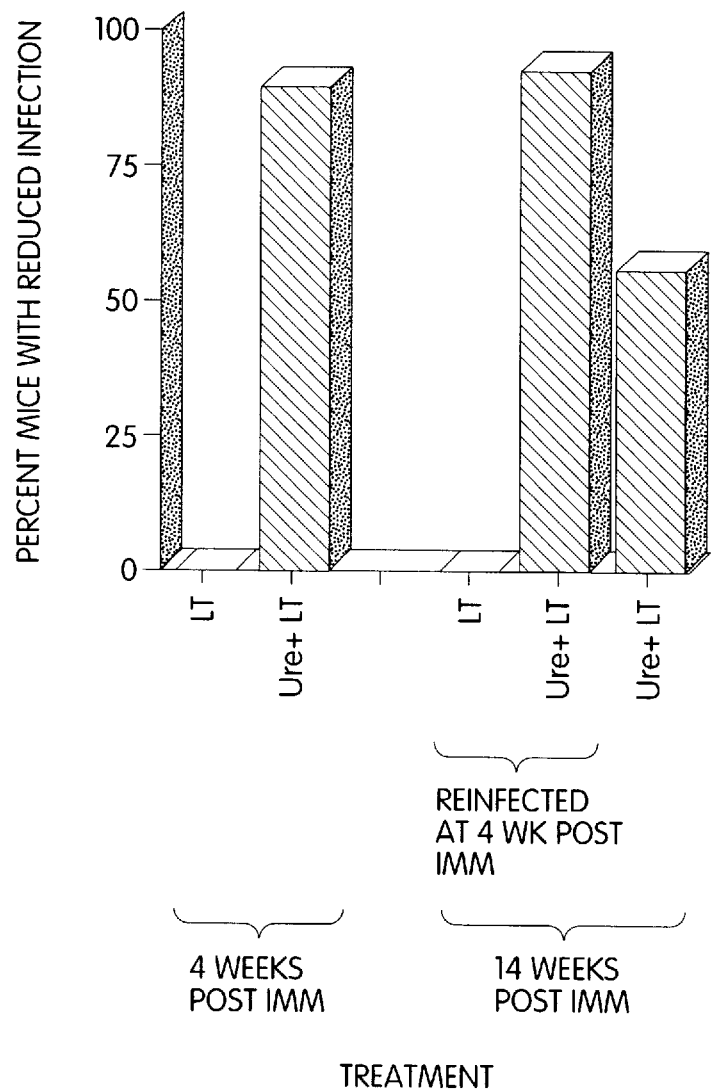
FIG. 12 is a graph showing that immunization of mice with rUrease +10 μg LT reduces or eradicates established H. felis infection. When these animals were reinfected with H. felis, they were protected against challenge.

The ability of recombinant urease vaccine to cure infection in mice was evaluated by intragastrically infecting Balb/c mice with 10$^7$ H. felis (FIG. 12). Four weeks after infection, groups of infected mice were given four weekly oral doses of 100 μg recombinant urease with 10 μg LT. Controls received LT only.

Ten of the mice in each group were necropsied four weeks after the final immunization to examine the degree of Helicobacter infection by quantitative gastric urease. Four weeks after immunization, nine of ten Balb/c mice (90%) were free from infection as measured by quantitative urease assay, whereas all controls were infected.

At four weeks, twelve animals receiving LT and 40 animals receiving urease+LT were reinfected with *H. felis*. Ten weeks after the challenge, the twelve animals receiving LT and 40 animals receiving Urease+LT were reinfected with *H. felis*. Ten weeks after this challenge, animals were sacrificed to determine the extent of infection by quantitative urease assay. Of the nine animals which were given urease+LT, but not subjected to reinfection, 5 were protected (57%), as determined by gastric urease activity. All twelve LT treated animals which were rechallenged were infected. Thirty seven of the 40 mice (93%) which were given urease+LT, and then re-challenged with *H. felis*, were protected as determined by reduced gastric urease activity. This experiment shows that urease vaccination not only eradicates an existing Helicobacter infection, but also protects the host against reinfection.

Five of fourteen (36%) immunized Swiss-Webster mice were cured or had reduced infections, whereas all control animals were infected, although the differences in infection ratios between groups was not significant (p=0.26, Fisher's exact test, two-tailed). Infection in Swiss-Webster mice was more severe than in Balb/c mice, as measured by higher mean gastric urease activity in unimmunized animals (p<0.0001, one-way ANOVA), possibly explaining the lower cure rates in Swiss-Webster versus Balb/c mice. Differences in susceptibility of mouse strains to *H. felis* has been noted (Sakagami et al., *Am. J. Gastroenterol* 89:1345, 1994).

By histologic assessment, all unimmunized Balb/c mice had 4+ infections (>100 bacteria/section), whereas reduced bacterial scores were seen in 43% of immunized mice at four weeks. At ten weeks, four of six had reduced urease activity, although only one of six had a reduced bacterial score.

The role of antibodies in Helicobacter therapy

The role of anti-urease antibodies in Helicobacter therapy, i.e., the clearance of *H. felis* from infected mice, was examined by first infecting Balb/c mice with $10^7$ *H. felis*. Four weeks after infection, the mice were orally immunized with 200 μg recombinant urease plus 10 μg CT. Control mice were given 10 μg CT only. Antigen was administered 4 times at one week intervals. Animals were sacrificed 4 and 10 weeks after the last immunization, and serum and fecal samples were collected for ELISA.

Figure 13:
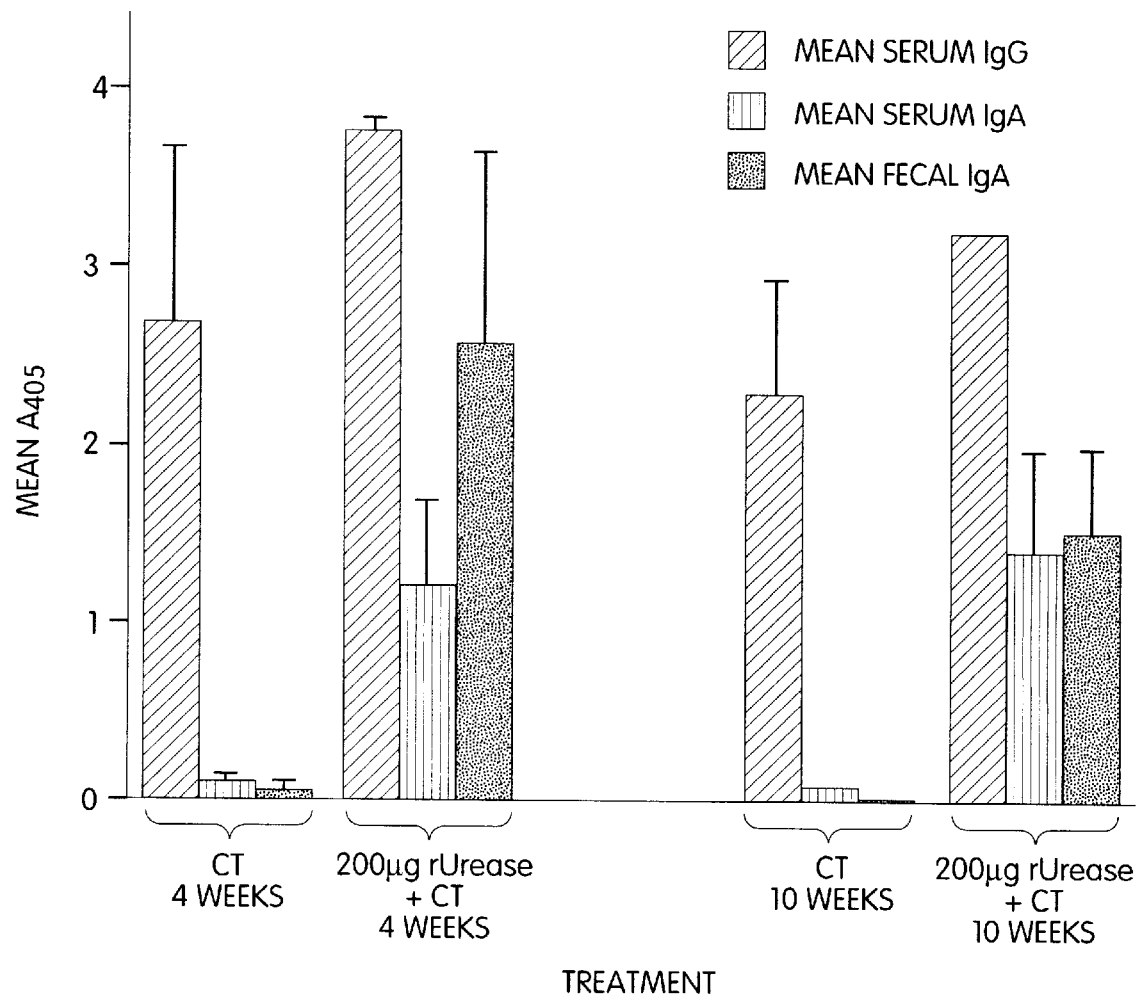
FIG. 13 is a graph showing the mean antibody response of mice 4 and 10 weeks after therapeutic immunization with either recombinant H. pylori urease and CT, or CT alone.

Mice infected with *H. felis* produced serum anti-urease IgG antibodies, but no secretory anti-urease IgA response was detected. However, infected animals immunized with urease/CT exhibited high secretory anti-urease IgA antibody responses (FIG. 13). There was no significant difference in urease specific mucosal IgA levels between immunized mice that remained infected and those with reduced bacterial scores.

These data indicate that *H. felis* infection does not elicit a secretory anti-urease response. Thus, suppression of the IgA antibody response may play a role in *H. felis's* ability to evade clearance by the immune system. In contrast, immunization of *H. felis*-infected mice with urease and a mucosal adjuvant resulted in strong mucosal anti-urease responses, which correlated with clearance of the infection *H. felis*.

Correlation of protection to Helicobacter infection with gastric immune responses Several of the experiments with the mouse infection model showed that some animals rendered resistant to infection by recombinant urease vaccine lacked detectable antibody responses or had low antibody levels in serum, saliva, or feces. Therefore, the immune response was measured in the gastric mucosa itself to determine if such measurements could be more precisely correlated with protection.

Immune responses in gastric mucosa were assessed by detecting IgA antibodies and IgA+ antibody secreting cells in intestinal and gastric murine tissue by immunohistochemistry. Portions of the stomach comprising pylorus-proximal duodenum, antrum, corpus, and cardia were mounted in OCT compound, flash-frozen, and cryosectioned. Sections (7 μm thick) were fixed in cold acetone, and IgA+ cells were identified by staining with biotinylated monoclonal anti-IgA, followed by avidin conjugated to biotinylated glucose oxidase (ABC-GO, Vector Laboratories), and counterstained with methyl green. Urease-specific antibody secreting cells (ASC) were identified by sequentially incubating sections with recombinant urease, rabbit anti-urease, biotinylated donkey anti-rabbit Ig (Amersham, Arlington Heights, Ill.), ABC-GO, TNBT, and methyl green. Control sections were incubated without urease or urease plus rabbit anti-urease to determine reactivity with the donkey secondary reagent and background endogenous glucose oxidase activity. Cryosections of cell pellets from an IgA hybridoma against *H. felis* ureB (MAB71, S. Czinn, Case-Western Reserve University) and an irrelevant IgA monoclonal (HNK20) against F glycoprotein of respiratory syncytial virus served as positive and negative controls, respectively.

Swiss-Webster mice were immunized orally with four weekly doses of 100 μg recombinant urease plus adjuvant (CT). Control mice received adjuvant only. Groups of three mice each were necropsied at 3, 7, 14, or 21 days after the last immunization. Peyer's patches were removed from the intestines and lamina propria lymphocytes (LPL) were isolated separation on a 40–70% Percoll gradient. IgA+ B cells were detected by ELISPOT assays in 96-well filter plates coated with 1 μg/well recombinant urease and blocked with bovine serum albumin. Ten-fold serial dilutions of LPL were added to the wells, starting at $1\times10^6$ cells. IgA+ ASC were detected with a biotinylated anti-mouse IgA reagent followed by streptavidin-alkaline phosphatase, and positive cells were counted by microscopy.

Anti-urease IgA+ ASC were found by ELISPOT in intestinal lamina propria as early as three days after the last immunization, peaked at seven days, and diminished thereafter (Table 8). Urease-specific ASC represented ~10% of the total IgA+ cells observed on immunohistochemistry. Two-color immunofluorescence microscopy confirmed that urease-specific ASC were also IgA+. These observations confirm that an intense anti-urease IgA response occurs at the level of the intestinal mucosa after oral antigenic stimulation. The chronology and kinetics of this response are similar to those described for other oral vaccines (Czerkinsky et al., *Infect. Immun.* 59:996–1001, 1991; McGhee & Kiyono, 1993, ibid.)

TABLE 8

Kinetics of induction of anti-urease IgA secreting cells after oral immunization with recombinant urease

| IMMUNIZATION | NUMBER OF ASC/$10^6$ LAMINA PROPRIA LYMPHOCYTES | | | |
| --- | --- | --- | --- | --- |
| | DAY 3[a] | DAY 7 | DAY 14 | DAY 21 |
| recombinant urease + CT[b] | 17[c] | 7400 | 10 | 2 |
| PBS + CT | 1 | 200 | 0 | 0 |

[a]Day after the last oral immunization.
[b]Cholera toxin.
[c]Average value from duplicate wells containing intestinal lymphocytes from three separate mice.

To determine whether IgA+ cells are recruited into the gastric mucosa, stomachs of orally immunized mice were examined by immunohistochemistry, as described above. IgA+ cells were virtually absent in gastric mucosa of immunized and control mice, indicating that the stomach is immunologically "silent" until stimulated by Helicobacter challenge.

The role of the stomach as an immunological effector organ in challenged, immunized mice was examined. Mice were given four weekly oral doses of 200 μg recombinant urease with 10 μg CT. Control mice received CT only. One week after immunization, the mice were challenged. Mice were necropsied prior to challenge and at 7, 14, 28, 70, and 133 days after challenge.

Figure 14:
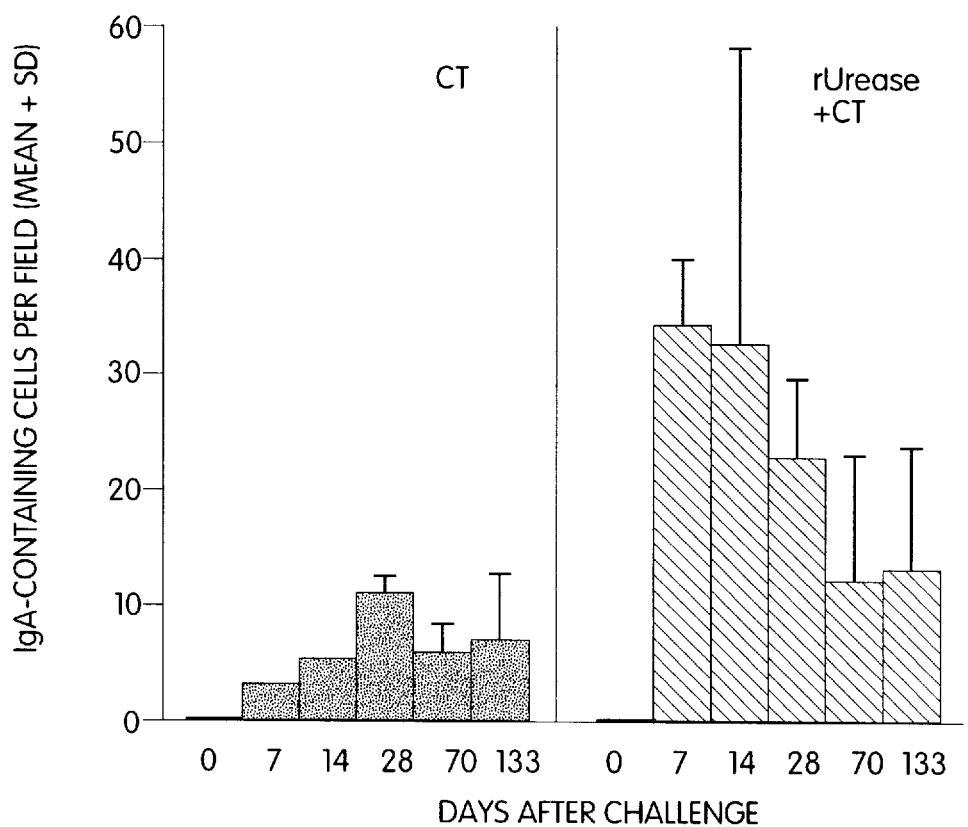
FIG. 14 is a graph showing numbers of IgA antibody secreting cells in gastric mucosa of immunized and unimmunized mice before, and at intervals after, infection with H. felis.

Prior to challenge, no IgA+ ASC were found. At all time intervals after challenge, IgA+ ASC were present in large numbers in the gastric mucosae of immunized mice, with a peak at seven days (FIG. 14). The number of IgA+ ASC greatly exceeded that in unimmunized (CT only) mice, especially 7–28 days after challenge. The anatomical localization of IgA+ ASC also differed, with immunized mice having cells throughout the mucosa, in the lamina propria, and around the crypts, but rarely under the surface epithelium. Urease-specific and IgA+ASC revealed that the majority of urease-specific cells in gastric mucosa were IgA+.

These observations indicate that the gastric mucosa of hosts primed by prior immunization becomes immunologically activated only after antigenic stimulation by H. felis. The resulting tissue response is characterized by rapid, intense, and long-lasting recruitment of IgA+ B cells, many of which are urease specific. This response is quantitatively greater than in immunologically naive mice after challenge. Moreover, the localization of IgA+ cells in immunized mice differs from that seen in immunologically naive mice that are challenged and become persistently infected with H. felis. The enhanced IgA+ ASC response in gastric mucosa suggests a basis for the protection conferred by immunization against H. felis challenge. The data are concordant with studies of cholera vaccine, in which immunological memory responses triggered within hours after bacterial challenge were sufficient to provide protection (Lycke & Holmgren, Scand. J. Immunol. 25:407–412, 1987).

Correlation of the gastric immune response and bacterial load

The relationship between the gastric tissue immune response and bacterial infection was defined at the structural level. Swiss-Webster mice were immunized with 4 weekly doses of 200 μg recombinant urease with 10 μg CT. One week after the last immunization, the mice were challenged with $10^7$ H. felis. Animals were sacrificed 0, 1, 7, 14, 28, 70, and 133 days after challenge, and H. felis colonization was assessed by light and electron microscopy.

Figure 15:
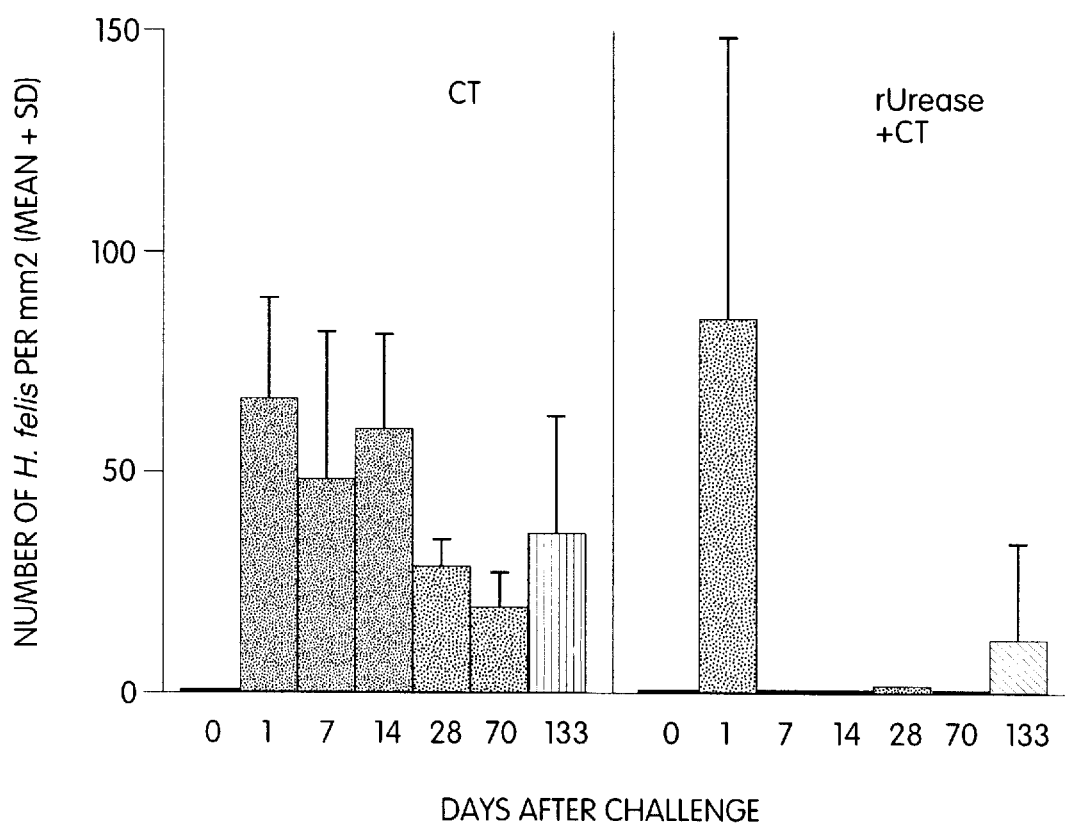
FIG. 15 is a graph showing the clearance of H. felis infection in mice previously immunized with recombinant H. pylori urease and CT.

Within 24 hours after challenge, both immunized and unimmunized mice had substantial numbers of H. felis within the lumen of gastric pits (FIG. 15). Within seven days after challenge, the bacteria were cleared from the immunized mice, but were still present in high numbers in the gastric pits and the lumens of unimmunized mice. Bacteria were also associated with the apical membrane of mucus-secreting cells of the unimmunized mice. The clearance of bacteria from the gastric mucosa of immunized mice corresponded to the appearance of IgA+ ASC and anti-urease ASC in the gastric tissue.

These results suggest the following sequence of events: 1) challenge of immunized mice results in transient colonization of gastric epithelium with H. felis; 2) unimmunized animals remain infected, while animals immunized with recombinant urease clear the bacteria from the stomach during the first week after challenge; and 3) clearance of infection is associated with the recruitment of IgA+ urease-specific ASC to gastric mucosa. A similar mechanism may be responsible for the clearance of bacteria from the gastric mucosa of chronically infected animals that are subjected to therapeutic immunization.

Antigenic conservation of urease among strains of H. pylori

The ability of various antisera to bind multiple clinical isolates of H. pylori was tested. The antisera included MPA3, a hyperimmune rabbit serum prepared against purified H. pylori urease, and sera and secretions (gastric wick samples and saliva) from mice immunized with recombinant urease. Antibody preparations were tested by immunoblotting for recognition of the homologous H. pylori strain (Hp630), ATCC 43504 type strain, and five clinical isolates from ulcer patients at St. Bartholomew's Hospital, London, collected within the last five years.

All antisera recognized the UreA and UreB subunits of all H. pylori strains, as well as purified native and recombinant H. pylori ureases, native and recombinant H. felis urease, and native H. mustelae urease. In addition, urease-specific IgA antibodies in gastric secretions and saliva of immunized mice reacted with both UreA and UreB of all H. pylori strains, as well as heterologous ureases. Immunologic recognition was greater for UreB than for UreA. Sham-immunized mice showed no reactivity with any urease subunits. These results demonstrate that H. pylori strains express ureases that are highly conserved at the antigenic level. Thus, antigenic variation among H. pylori strains is not a significant factor for development of a recombinant urease vaccine.

Identification of human patients for administration of recombinant H. pylori urease vaccine The recombinant H. pylori urease vaccine of the invention may be administered to uninfected individuals as a prophylactic therapy or to individuals infected with Helicobacter as an antibacterial therapy. Individuals selected for prophylactic administration of recombinant urease include any individual at risk of Helicobacter infection as based upon age, geographical location, or the presence of a condition which renders the individual susceptible to Helicobacter infection. Individuals at particularly high risk of infection, or who would be most severely affected by infection, include individuals in developing countries, infants and children in developing and in developed countries, individuals with naturally or artificially low gastric acid pH, submarine crews, and military personnel.

Individuals who may receive the recombinant H. pylori urease vaccine as a therapeutic include those individuals with symptoms of gastritis or other gastrointestinal disorders which may be associated with H. pylori infection. The clinical symptoms associated with gastritis, an inflammation of the stomach mucosa, include a broad range of poorly-defined, and generally inadequately treated, symptoms such as indigestion, "heart burn," dyspepsia, and excessive eructation. A general discussion of gastritis appears in Sleisenger and Fordtran, In *Gastrointestinal Disease,* 4th Ed., Saunders Publishing Co., Philadelphia, Pa., pp. 772–902, 1989.

Individuals who have a gastrointestinal disorder may also be treated by administration of the vaccine of the invention. Gastrointestinal disorders includes any disease or other disorder of the gastrointestinal tract of a human or other mammal. Gastrointestinal disorders include, for example, disorders not manifested by the presence of ulcerations in the gastric mucosa (non-ulcerative gastrointestinal disorder), including chronic or atrophic gastritis, gastroenteritis, non-ulcer dyspepsia, esophageal reflux disease, gastric motility disorders, and peptic ulcer disease (e.g., gastric and duodenal ulcers). Peptic ulcers involve ulceration and formation of lesions of the mucous membrane of the esophagus, stomach, or duodenum, and is generally characterized by loss of tissue due to the action of digestive acids, pepsin, or other factors. Alternatively, it may be desirable to administer the vaccine to asymptomatic individuals, particularly where the individual may have been exposed to *H. pylori* or has a condition rendering the individual susceptible to infection.

Infection with Helicobacter can be readily diagnosed by a variety of methods well known in the art, including, e.g., by serology, $^{13}$C breath test, and/or gastroscopic examination. Preparation of purified recombinant urease for administration to patients The process for formulation of recombinant urease involves combination of the urease with a stabilizer, (e.g., a carbohydrate mannitol) and freeze drying (i.e., lyophilizing) the product. This process prevents degradation by aggregation and fragmentation. In addition, the product is stable for months following lyophilization. The mechanism for instability involves formation of disulfide bonds between protein subunits and is effectively inhibited by lyophilization.

Recombinant urease is freeze-dried following the final purification step. The purified protein product (approximately 4 mg/ml) is dialyzed against 2% sucrose, and this solution is transferred to lyophilization vials. The vialed solution is either: (1) frozen in liquid nitrogen, and then placed into the lyophilizer, or (2) cooled to 4° C., and then placed in the lyophilizer, where it is frozen to −40° C., or lower. Lyophilization is carried out using standard methods. The freeze-dried product may be reconstituted in water.

Mode of administration to human patients

Recombinant *H. pylori* urease is administered to a mucosal surface of the individual in order to stimulate a mucosal immune response effective to provide protection to subsequent exposure to Helicobacter and/or facilitate clearance of a pre-existing Helicobacter infection. Preferably, recombinant urease is administered so as to elicit a mucosal immune response associated with production of anti-urease IgA antibodies and/or infiltration of lymphocytes into the gastric mucosa. The recombinant urease may be administered to any mucosal surface of the patient. Preferable mucosal surfaces are intranasal or oral. In the case of oral administration, it is preferable that the administration involves ingestion of the vaccine, but the vaccine may also be administered as a mouth wash, so that an immune response is stimulated in the mucosal surface of the oral cavity, without actual ingestion of the vaccine. Alternatively, a systemic mucosal immune response may be achieved by administration of the vaccine to a mucosal surface of the eye in the form of, e.g., an eye drop or an intraocular implant.

Dosages of recombinant *H. pylori* urease administered to the individual as either a prophylactic therapy or an antibacterial therapy can be determined by one skilled in the art. Generally, dosages will contain between about 10 μg to 1,000 mg, preferably between about 10 mg and 500 mg, more preferably between about 30 mg and 120 mg, more preferably between about 40 mg and 70 mg, most preferably about 60 mg recombinant *H. pylori* urease.

At least one dose of the recombinant *H. pylori* urease will be administered to the patient, preferably at least two doses, more preferably four doses, with up to six or more total doses administered. It may be desirable to administer booster doses of the recombinant urease at one or two week intervals after the last immunization, generally one booster dose containing less than, or the same amount of, recombinant *H. pylori* urease as the initial dose administered. Most preferably, the vaccine regimen will be administered in four doses at one week intervals.

Recombinant *H. pylori* urease may be co-administered with a mucosal adjuvant. The mucosal adjuvant may be any mucosal adjuvant known in the art which is appropriate for human use. For example, the mucosal adjuvant may be cholera toxin (CT), enterotoxigenic *E. Coli* heat-labile toxin (LT), or a derivative, subunit, or fragment of CT or LT which retains adjuvanticity. Preferably, the mucosal adjuvant is LT or a derivative of LT. The mucosal adjuvant is co-administered with recombinant *H. pylori* urease in an amount effective to elicit or enhance a mucosal immune response, particularly a humoral and/or a mucosal immune response. The ratio of adjuvant to recombinant urease may be determined by standard methods by one skilled in the art. Preferably, the adjuvant is present at a ratio of 1 part adjuvant to 10 parts recombinant urease.

A buffer may be administered prior to administration of recombinant *H. pylori* urease in order to neutralize or increase the pH of the gastric acid. Any buffer that is effective in raising the pH of gastric acid and is appropriate for human use may be used. For example, buffers such as sodium bicarbonate, potassium bicarbonate, and sodium phosphate may be used. Preferably, oral administration of the vaccine is buffer-free, i.e., no amount of a pH-raising buffer compound effective to significantly affect gastric acid pH is administered to the patient either prior to, or concomitant with, administration of recombinant urease.

The vaccine formulation containing recombinant urease may contain a variety of other components, including stabilizers, flavor enhancers (e.g., sugar), or, where the vaccine is administered as an antibacterial therapeutic, other compounds effective in facilitating clearance and/or eradication of the infecting bacteria.

For prophylactic therapy, the vaccine containing recombinant *H. pylori* urease may be administered at any time prior to contact with, or establishment of, Helicobacter infection. Because the vaccine can also act as an antibacterial therapy, there is no contraindication for administration of the vaccine if there is marginal evidence or suspicion of a pre-existing Helicobacter infection (e.g., an asymptomatic infection).

For use of the vaccine as an antibacterial therapy, recombinant *H. pylori* urease may be administered at any time before, during, or after the onset of symptoms associated with Helicobacter infection or with gastritis, peptic ulcers or other gastrointestinal disorder. Although it is not a prerequisite to the initiation of therapy, it may be preferable to confirm diagnosis of Helicobacter infection by $^{13}$C breath test, serology, gastroscopy, biopsy, or another Helicobacter detection method known in the art.

The progress of immunized patients may be followed by general medical evaluation, screening for *H. pylori* infection by serology, $^{13}$C breath test, and/or gastroscopic examination.

Example of human administration of recombinant *H. pylori* urease

A vaccine composed of 60 mg of recombinant *H. pylori* urease in a total volume of 15 ml of water containing 2% w/v sucrose, pH 7.5 is orally administered to the patient. Administration of the vaccine is repeated at weekly intervals for a total of 4 doses. Symptoms are recorded daily by the patient. To determine adverse effects, physician interviews are performed weekly during the period of vaccine administration, as well as 1 week and 1 month after the last immunization. Anti-urease antibodies are measured in serum and saliva, and antibody-secreting cells are monitored in peripheral blood collected 7 days after the last immunization.

What is claimed is:

1. A method of treating *Helicobacter pylori* infection in a patient, said method comprising administering to a mucosal surface of said patient an immunogenically effective amount of a composition comprising multimeric complexes of recombinant, enzymatically inactive Helicobacter urease.

2. The method of claim 1, wherein said composition comprises multimeric complexes comprising eight Urease A subunits and eight Urease B subunits, multimeric complexes comprising six Urease A subunits and six Urease B subunits, and/or multimeric complexes comprising four Urease A subunits and four Urease B subunits.

3. The method of claim 2, wherein said composition comprises multimeric complexes comprising eight Urease A subunits and eight Urease B subunits, multimeric complexes comprising six Urease A subunits and six Urease B subunits, and multimeric complexes comprising four Urease A subunits and four Urease B subunits.

4. The method of claim 1, wherein said mucosal surface is nasal.

5. The method of claim 1, wherein said mucosal surface is oral.

6. The method of claim 1, wherein said composition is administered without gastric neutralization.

7. The method of claim 1, wherein said multimeric complex is administered in association with a mucosal adjuvant.

8. The method of claim 7, wherein said mucosal adjuvant is heat-labile enterotoxin of enterotoxigenic *Escherichia coli*, or a derivative thereof.

9. The method of claim 7, wherein the mucosal adjuvant is cholera toxin, or a derivative thereof.

10. The method of claim 1, wherein said multimeric complexes of recombinant, enzymatically inactive Helicobacter urease are freeze-dried before administration.

* * * * *